US011654164B2

(12) United States Patent
Jones et al.

(10) Patent No.: US 11,654,164 B2
(45) Date of Patent: *May 23, 2023

(54) MICROBIOTA RESTORATION THERAPY (MRT) COMPOSITIONS AND METHODS OF MANUFACTURE

(71) Applicant: REBIOTIX, INC., Roseville, MN (US)

(72) Inventors: Lee A. Jones, Fridley, MN (US);
Courtney R. Jones, Fridley, MN (US);
Beth Anne-Szkudlarek Brown, Plymouth, MN (US); Joshua Erickson, Champlin, MN (US)

(73) Assignee: REBIOTIX, INC., Roseville, MN (US)

( * ) Notice: Subject to any disclaimer, the term of this patent is extended or adjusted under 35 U.S.C. 154(b) by 167 days.

This patent is subject to a terminal disclaimer.

(21) Appl. No.: 17/152,459

(22) Filed: Jan. 19, 2021

(65) Prior Publication Data
US 2021/0138000 A1 May 13, 2021

Related U.S. Application Data

(63) Continuation of application No. 15/827,732, filed on Nov. 30, 2017, now Pat. No. 10,905,726, which is a continuation of application No. 15/178,176, filed on Jun. 9, 2016, now Pat. No. 10,226,431.

(60) Provisional application No. 62/247,825, filed on Oct. 29, 2015, provisional application No. 62/173,182, filed on Jun. 9, 2015.

(51) Int. Cl.
A61K 35/74 (2015.01)
A61K 9/48 (2006.01)
A61K 9/19 (2006.01)
A61K 35/00 (2006.01)

(52) U.S. Cl.
CPC ............... A61K 35/74 (2013.01); A61K 9/19 (2013.01); A61K 9/4808 (2013.01); A61K 9/4816 (2013.01); A61K 9/4858 (2013.01); A61K 9/4866 (2013.01); A61K 2035/11 (2013.01)

(58) Field of Classification Search
CPC ........ A61K 35/74; A61K 9/19; A61K 9/4808; A61K 9/4816; A61K 9/4858; A61K 9/4866; A61K 2035/11
See application file for complete search history.

(56) References Cited

U.S. PATENT DOCUMENTS

| | | | |
|---|---|---|---|
| 3,317,675 A | 5/1967 | Harris et al. | |
| 5,196,205 A | 3/1993 | Borody | |
| 5,229,374 A | 7/1993 | Burton et al. | |
| 5,274,001 A | 12/1993 | Borody | |
| 5,443,826 A | 8/1995 | Borody | |
| 5,476,669 A | 12/1995 | Borody | |
| 5,519,014 A | 5/1996 | Borody | |
| 5,599,795 A | 2/1997 | McCann et al. | |
| 5,711,446 A | 1/1998 | Jeffs et al. | |
| 5,858,403 A | 1/1999 | Borody et al. | |
| 5,925,354 A | 7/1999 | Fuller et al. | |
| 6,096,310 A | 8/2000 | Bier | |
| 6,103,268 A | 8/2000 | Borody et al. | |
| 6,132,767 A | 10/2000 | Borody et al. | |
| 6,214,341 B1 | 4/2001 | Thomas, Jr. et al. | |
| 6,426,338 B1 | 7/2002 | Borody | |
| 6,428,783 B1 | 8/2002 | Khachatrian et al. | |
| 6,635,260 B1 | 10/2003 | Gerdin | |
| 6,645,530 B1 | 11/2003 | Borody | |
| 6,680,168 B2 | 1/2004 | Thomas, Jr. et al. | |
| 6,805,852 B2 | 10/2004 | Lin et al. | |
| 6,861,053 B1 | 3/2005 | Lin et al. | |
| 6,969,520 B2 | 11/2005 | Thomas, Jr. et al. | |
| 7,048,906 B2 | 5/2006 | Lin et al. | |
| 7,125,708 B2 | 10/2006 | Wynne et al. | |
| 7,307,062 B2 | 12/2007 | Bolte | |
| 7,607,776 B1 | 10/2009 | Lewis et al. | |
| 7,993,682 B2 | 8/2011 | Borody et al. | |
| 8,058,418 B2 | 11/2011 | Boyle et al. | |
| 8,110,177 B2 | 2/2012 | Lin et al. | |
| 8,460,648 B2 | 6/2013 | Borody | |
| 8,772,242 B2 | 7/2014 | Von Maltzahn et al. | |
| 8,906,668 B2 | 12/2014 | Henn et al. | |

(Continued)

FOREIGN PATENT DOCUMENTS

| CA | 1330759 C | 7/1994 |
|---|---|---|
| CA | 1333564 C | 12/1994 |

(Continued)

OTHER PUBLICATIONS

Aas, J., et al., "Recurrent Clostridium Difficile Colitis: Case Series Involving 18 Patients Treated with Donor Stool Administered Via a Nasogastric Tube", Clinical Infectious Diseases, vol. 36, Mar. 1, 2003, pp. 580-585, Infectious Diseases Society of America.

Aas, J., et al., "Stool Transplantation for Older Patients with Clostridium Difficile Infection", Jags, vol. 57, No. 12, Dec. 2009, pp. 2386-2387.

Abujamel, T., et al., "Defining the Vulnerable Period for Re-Establishment of Clostridium difficile Colonization after Treatment of C. difficile Infection with Oral Vancomycin or Metronidazole", PLOS One, vol. 8, Issue 10, Oct. 2013, pp. 1-12.

Allen-Vercoe, E., et al., "A Canadian Working Group Report on Fecal Microbial Therapy: Microbial Ecosystems Therapeutics", Can J Gastroenterol, vol. 26, No. 7, Jul. 2012, pp. 457-462, Pulsus Group Inc.

(Continued)

Primary Examiner — Irina S Zemel
(74) Attorney, Agent, or Firm — Foley & Lardner LLP

(57) ABSTRACT

Microbiota restoration therapy (MRT) compositions (e.g., oral MRT compositions) and methods for manufacturing MRT compositions are disclosed. An example method for manufacturing an MRT composition may include collecting a stool sample, purifying the stool sample to form a purified sample, stabilizing the purified sample to form a stabilized sample, converting the stabilized sample to a solid, adding one or more additives and/or excipients to the solid to form a treatment composition, and encapsulating the treatment composition.

17 Claims, 5 Drawing Sheets

(56) References Cited

U.S. PATENT DOCUMENTS

| | | |
|---|---|---|
| 9,433,651 B2 | 9/2016 | Jones et al. |
| 9,511,099 B2 | 12/2016 | Jones et al. |
| 9,511,100 B2 | 12/2016 | Jones et al. |
| 9,642,880 B2 | 5/2017 | Jones et al. |
| 9,675,648 B2 | 6/2017 | Jones et al. |
| 9,694,039 B2 | 7/2017 | Jones et al. |
| 9,782,445 B2 | 10/2017 | Jones et al. |
| 10,226,431 B2 | 3/2019 | Jones et al. |
| 10,383,901 B2 | 8/2019 | Jones et al. |
| 10,391,064 B2 | 8/2019 | Jones et al. |
| 10,391,129 B2 | 8/2019 | Jones et al. |
| 10,434,124 B2 | 10/2019 | Jones et al. |
| 10,434,125 B2 | 10/2019 | Jones et al. |
| 10,434,126 B2 | 10/2019 | Jones et al. |
| 10,471,107 B2 | 11/2019 | Jones et al. |
| 10,493,111 B2 | 12/2019 | Jones et al. |
| 10,603,341 B2 | 3/2020 | Jones et al. |
| 10,610,547 B2 | 4/2020 | Jones et al. |
| 10,624,932 B2 | 4/2020 | Jones et al. |
| 10,688,137 B2 | 6/2020 | Jones et al. |
| 10,799,539 B2 | 10/2020 | Jones et al. |
| 10,828,340 B2 | 11/2020 | Jones et al. |
| 10,905,726 B2 | 2/2021 | Jones et al. |
| 2002/0022019 A1 | 2/2002 | Lauland |
| 2003/0031659 A1 | 2/2003 | Farmer |
| 2003/0154105 A1 | 8/2003 | Ferguson |
| 2003/0161871 A1 | 8/2003 | Hird et al. |
| 2003/0180260 A1 | 9/2003 | Clancy et al. |
| 2004/0028689 A1 | 2/2004 | Borody |
| 2004/0062757 A1 | 4/2004 | Finegold |
| 2004/0167062 A1 | 8/2004 | Bolte |
| 2004/0170617 A1 | 9/2004 | Finegold |
| 2004/0265291 A1 | 12/2004 | Drake et al. |
| 2005/0074441 A1 | 4/2005 | Collins et al. |
| 2005/0103678 A1* | 5/2005 | Clark .............. B29C 65/7443 206/538 |
| 2005/0209883 A1 | 9/2005 | Fletcher-Haynes et al. |
| 2005/0239706 A1 | 10/2005 | Backhed et al. |
| 2005/0271749 A1 | 12/2005 | Borody et al. |
| 2006/0008511 A1 | 1/2006 | Lin et al. |
| 2006/0029608 A1 | 2/2006 | Thomas, Jr. et al. |
| 2006/0160121 A1 | 7/2006 | Mounts et al. |
| 2006/0210448 A1 | 9/2006 | Wang et al. |
| 2006/0257471 A1* | 11/2006 | Ettema .............. C07D 215/227 424/464 |
| 2007/0178078 A1 | 8/2007 | Khoo |
| 2007/0231336 A1 | 10/2007 | Thomas, Jr. et al. |
| 2008/0008751 A1* | 1/2008 | Fox .................. A61K 9/2077 424/464 |
| 2008/0027353 A1 | 1/2008 | Kliman |
| 2008/0075901 A1* | 3/2008 | Lee .................. B29C 48/07 428/521 |
| 2008/0254009 A1 | 10/2008 | Finegold |
| 2008/0269258 A1 | 10/2008 | Breaker et al. |
| 2009/0148540 A1 | 6/2009 | Martin et al. |
| 2009/0305253 A1 | 12/2009 | Breaker et al. |
| 2010/0008850 A1 | 1/2010 | Martin |
| 2010/0151019 A1* | 6/2010 | Ramani ............... A61K 9/0065 424/465 |
| 2010/0172874 A1 | 7/2010 | Turnbaugh et al. |
| 2010/0316617 A1 | 12/2010 | Renaud et al. |
| 2011/0123501 A1 | 5/2011 | Chou et al. |
| 2011/0129529 A1 | 6/2011 | Lin |
| 2011/0177976 A1 | 7/2011 | Gordon et al. |
| 2011/0200570 A1 | 8/2011 | Mosbaugh et al. |
| 2011/0223252 A1 | 9/2011 | Borody et al. |
| 2011/0240511 A1* | 10/2011 | Bolton .............. A61J 1/035 206/532 |
| 2012/0252775 A1 | 10/2012 | Finegold |
| 2012/0276059 A1 | 11/2012 | Boone et al. |
| 2012/0276060 A1 | 11/2012 | Boone et al. |
| 2013/0022575 A1 | 1/2013 | Cassity |
| 2013/0045274 A1 | 2/2013 | Hlavka |
| 2013/0052172 A1 | 2/2013 | Baker |
| 2013/0064885 A1 | 3/2013 | Lin et al. |
| 2013/0108598 A1 | 5/2013 | Oresic et al. |
| 2013/0149339 A1 | 6/2013 | Honda et al. |
| 2013/0195804 A1 | 8/2013 | Borody |
| 2013/0195820 A1 | 8/2013 | Wacklin et al. |
| 2013/0266539 A1 | 10/2013 | Borody |
| 2014/0147417 A1 | 5/2014 | Sadowsky et al. |
| 2014/0147425 A1 | 5/2014 | Henn et al. |
| 2014/0199281 A1 | 7/2014 | Henn et al. |
| 2014/0219966 A1 | 8/2014 | Boone et al. |
| 2014/0234260 A1 | 8/2014 | Borody |
| 2014/0238154 A1 | 8/2014 | Stevens |
| 2014/0255351 A1 | 9/2014 | Berstad et al. |
| 2014/0328803 A1 | 11/2014 | McKenzie et al. |
| 2014/0363397 A1 | 12/2014 | Allen-Vercoe et al. |
| 2014/0363400 A1* | 12/2014 | Jones .............. C12N 1/20 424/93.4 |
| 2015/0037285 A1 | 2/2015 | Blaser et al. |
| 2015/0050246 A1 | 2/2015 | Jones et al. |
| 2015/0093360 A1 | 4/2015 | McKenzie et al. |
| 2016/0339065 A1 | 11/2016 | Adams et al. |
| 2016/0361263 A1 | 12/2016 | Jones et al. |
| 2019/0365831 A1 | 12/2019 | Jones et al. |
| 2020/0230182 A1 | 7/2020 | Jones et al. |
| 2021/0137999 A1 | 5/2021 | Jones et al. |

FOREIGN PATENT DOCUMENTS

| | | |
|---|---|---|
| CA | 1337265 C | 10/1995 |
| CA | 2189418 A1 | 5/1997 |
| CA | 2289717 A1 | 11/1997 |
| CA | 2232001 C | 12/2002 |
| CA | 2090220 C | 7/2003 |
| CA | 2478135 A1 | 9/2003 |
| CA | 2582137 A1 | 2/2007 |
| CA | 2289717 C | 2/2009 |
| CA | 2189418 C | 7/2011 |
| CN | 1444484 A | 9/2003 |
| CN | 101016527 A | 8/2007 |
| CN | 102159084 A | 8/2011 |
| CN | 104922158 A | 9/2015 |
| CN | 105103858 A | 12/2015 |
| DE | 3889547 T2 | 11/1994 |
| DE | 68928665 T2 | 11/1998 |
| EP | 0433299 A1 | 6/1991 |
| EP | 0397689 B1 | 5/1994 |
| EP | 0771562 A3 | 5/1997 |
| EP | 1300472 A1 | 4/2003 |
| EP | 0554291 B1 | 12/2003 |
| EP | 0952773 B1 | 11/2005 |
| EP | 0980246 B1 | 12/2006 |
| EP | 2030623 A1 | 3/2009 |
| EP | 1340078 B1 | 5/2009 |
| EP | 1432786 B1 | 7/2009 |
| EP | 0554291 B2 | 10/2010 |
| EP | 2243487 A1 | 10/2010 |
| EP | 2600877 A4 | 2/2012 |
| EP | 2636684 A1 | 9/2013 |
| JP | H07-023779 | 1/1995 |
| JP | 2001-327280 A | 11/2001 |
| JP | 2009022280 A | 2/2009 |
| JP | 2011500821 A | 1/2011 |
| JP | 2015502923 A | 1/2015 |
| JP | 201591647 A | 5/2015 |
| WO | 8903219 A1 | 4/1989 |
| WO | 8905659 A1 | 6/1989 |
| WO | 9001335 A1 | 2/1990 |
| WO | 9206690 A1 | 4/1992 |
| WO | 9611014 A1 | 4/1996 |
| WO | 9641615 A2 | 12/1996 |
| WO | 9709886 A1 | 3/1997 |
| WO | 9850043 A1 | 11/1998 |
| WO | 200197821 A1 | 12/2001 |
| WO | 2001093904 A1 | 12/2001 |
| WO | 200207741 A1 | 1/2002 |
| WO | 2003002713 A2 | 1/2003 |
| WO | 2003074061 A1 | 9/2003 |
| WO | 2007018563 A2 | 2/2007 |
| WO | 2008076696 A2 | 6/2008 |

(56) References Cited

FOREIGN PATENT DOCUMENTS

| | | |
|---|---|---|
| WO | 2009055362 A1 | 4/2009 |
| WO | 2009120347 A2 | 10/2009 |
| WO | 2010002890 A2 | 1/2010 |
| WO | 2010019208 A1 | 2/2010 |
| WO | 2011033310 A1 | 3/2011 |
| WO | 2011036539 A1 | 3/2011 |
| WO | 2011047439 A1 | 4/2011 |
| WO | 2011050397 A1 | 5/2011 |
| WO | 2011094027 A1 | 8/2011 |
| WO | 2011107481 A2 | 9/2011 |
| WO | 2011107482 A2 | 9/2011 |
| WO | 2012013861 A2 | 2/2012 |
| WO | 2012016287 A2 | 2/2012 |
| WO | 2012024638 A2 | 2/2012 |
| WO | 2012033814 A2 | 3/2012 |
| WO | 2012033814 A3 | 3/2012 |
| WO | 2012050513 A1 | 9/2012 |
| WO | 2012118535 A1 | 9/2012 |
| WO | 2012122478 A1 | 9/2012 |
| WO | 2012122522 A1 | 9/2012 |
| WO | 2012142605 A1 | 10/2012 |
| WO | 2012149351 A1 | 11/2012 |
| WO | 2012159023 A2 | 11/2012 |
| WO | 2013053836 A1 | 4/2013 |
| WO | 2013090825 A1 | 6/2013 |
| WO | 2013150331 A1 | 10/2013 |
| WO | 2013163582 A1 | 10/2013 |
| WO | 2013171515 A1 | 11/2013 |
| WO | 2014006532 A1 | 1/2014 |
| WO | 2014078911 A1 | 5/2014 |
| WO | 2014082050 A1 | 5/2014 |
| WO | 2014082132 A1 | 6/2014 |
| WO | 2014121298 A3 | 8/2014 |
| WO | 2014121301 A1 | 8/2014 |
| WO | 2014121302 A2 | 8/2014 |
| WO | 2014121302 A3 | 8/2014 |
| WO | 2014121304 A1 | 8/2014 |
| WO | 2014145958 A2 | 9/2014 |
| WO | 2014145958 A3 | 9/2014 |
| WO | 2014145958 A4 | 9/2014 |
| WO | 2014152484 A1 | 9/2014 |
| WO | 2014153194 A2 | 9/2014 |
| WO | 2014153194 A4 | 9/2014 |
| WO | 2014197562 A1 | 12/2014 |
| WO | 2015026235 A2 | 2/2015 |

OTHER PUBLICATIONS

Angelberger, S., et al., "Temporal Bacterial Community Dynamics Vary Among Ulcerative Colitis Patients after Fecal Microbiota Transplantation", American Journal of Gastroenterology, vol. 180, pp. 1620-1630, American College of Gastroenterology, 2013.

Arkkila, P.E., et al., "Fecal Bacteriotherapy for Recurrent Clostridium Difficile Infection", Gastroenterology Conference: Digestive Disease Week, May 2010, W.B. Saunders.

Austin, M., et al., "Fecal Microbiota Transplantation in the Treatment of Clostridium difficile Infections", The American Journal of Medicine (2014), doi: 10.1016/j.amjmed.2014.02.017 (15 pgs.).

Bahl, M.I., et al., "Freezing Fecal Samples Prior to DNA Extraction Affects the Firmicutes to Bacteroidetes Ratio Determined by Downstream Quantitative PCR Analysis", FEMS Microbiology Letters, vol. 329, 2012, pp. 193-197, Blackwell Publishing Ltd.

Bakken, J., et al., "Fecal Bacteriotherapy for Recurrent Clostridium difficile Infection", Anaerobe, vol. 15, Sep. 2009, pp. 285-289, Elsevier Ltd.

Bonfrate, L., et al., "Microbiota in Health and Irritable Bowel Syndrome: Current Knowledge, Perspectives and Therapeutic Options", Scandinavian Journal of Gastroenterology, vol. 48, 2013, pp. 995-1009, Informa Healthcare.

Borody, T.J., et al., "Bacteriotherapy Using Fecal Flora", J Clin Gastroenterol, vol. 38, No. 6, Jul. 2004, pp. 475-483, Lippincott Williams & Wilkins.

Borody, T.J., et al., "Bowel-Flora Alteration: A Potential Cure for Inflammatory Bowel Disease and Irritable Bowel Syndrome?", The Medical Journal of Australia, vol. 150, May 15, 1989, p. 604.

Borody, T.J., et al., "Fecal Microbiota Transplantation: Indications, Methods, Evidence, and Future Directions", Curr Gastroenterol Rep, vol. 15, No. 337, Jul. 14, 2013, pp. 1-7, Springer.

Borody, T.J., et al., "Therapeutic Faecal Microbiota Transplantation: Current Status and Future Developments", Current Opinion, vol. 30, No. 1, Jan. 2013, pp. 97-105, Lippincott Williams & Wilkins.

Borody, T.J., et al., "Treatment of Ulcerative Colitis Using fecal Bacteriotherapy", J Clin Gastroenterol, vol. 37, No. 1, 2003, pp. 42-47, Lippincott Williams & Wilkins.

Bowden, T., et al., "Pseudomembranous Enterocolitis: Mechanism of Restoring Floral Homeostasis", The American Surgeon, No. 4, Apr. 1981, pp. 178-183, J. R. Lippincott Company.

Brace, C., et al., "Microbial composition analysis of Clostridium difficile infections in an ulcerative colitis patient treated with multiple fecal microbiota transplantations", J Crohns Colitis (2014), http://dx.doi.org/10.1016/j.crohns.2014.01.020 (5 pgs.).

Brandt, L. et al., "American Journal of Gastroenterology Lecture: Intestinal Microbiota and the Role of Fecal Microbiota Transplant (FMT) in Treatment of C Diff Infection", The American Journal of Gastroenterology, vol. 108, Jan. 15, 2013, pp. 177-185, American College of Gastroenterology.

Brandt, L., et al., "An Overview of Fecal Microbiota Transplantation: Techniques, Indications and Outcomes", Gastrointestinal Endoscopy, vol. 78, No. 2, 2013, pp. 240-249, American Society for Gastrointestinal Endoscopy.

Brandt, L., et al., "Long-Term Follow-Up of Colonoscopic Fecal Microbiota Transplant for Recurrent Clostridium Difficile Infection", The American Journal of Gastroenterology, vol. 107, Mar. 27, 2012, pp. 1079-1087, American College of Gastroenterology.

Brandt, L., et al., "Norovirus Gastroenteritis After Fecal Microbiota Transplantation for Treatment of Clostridium difficile Infection Despite Asymptomatic Donors and Lack of Sick Contacts", The American Journal of Gastroenterology, vol. 108, Aug. 2013, pp. 1367-1368, American College of Gastroenterology.

Burke, K., et al., "Fecal Transplantation for Recurrent Clostridium Difficile Infection in Older Adults: A Review", JAGS, vol. 61, 2013, pp. 1394-1398, The American Geriatrics Society.

Cammarota, G., et al. "Fecal Microbiota Transplantation for the Treatment of Clostridium difficile Infection: A Systematic Review", Journal of Clinical Gastroenterology, 2014, pp. 1-10, Lippincott Williams & Wilkins.

Cammarota, G., et al. "Fecal Transplantation for Clostridium difficile Infection. Three Cases Treated in Italy", Digestive and Liver Disease, 2014, p. 1, Elsevier Ltd.

Cammarota, G., et al., "Gut microbiota modulation: probiotics, antibiotics or fecal microbiota transplantation?" Intern Emerg Med (2014), DOI: 10.1007/s11739-014-069-4 (9 pgs.).

Cardona, S., et al., "Storage Conditions of Intestinal Microbiota Matter in Metagenomic Analysis", BMC Microbiology, vol. 12, No. 158, 2012, pp. 1-8, BioMed Central Ltd.

Carroll, I., et al., "Characterization of the Fecal Microbiota Using High-Throughput Sequencing Reveals a Stable Microbial Community During Storage", PLOS One, vol. 7, Issue 10, Oct. 2012, pp. 1-7.

Collins, D., "Pseudomembranous Enterocolitis—Further Observations on the Value of Donor Fecal Enemata as an Adjunct in the Treatment of Pseudomembranous Enterocolitis", Journal of Proctology, vol. 11, No. 5, Oct. 1960, pp. 389-391.

Bakken, J., et al., "Treating Clostridium Difficile Infection with Fecal Microbiota Transplantation", Clinical Gastroenterology and Hepatology, vol. 9, No. 12, Dec. 2011, pp. 1044-1049.

Bakken, J., et al., "Treatment Approaches Including Fecal Microbiota Transplantation for Recurrent Clostridium diffiile Infection (RCDI) among Infectious Disease Physicians", Anaerobe, vol. 24, 2013, pp. 20-24, Elsevier Ltd.

Baron, T., "Fecal Microbiota Transplant: We Know It's History, But Can We Predict It's Future?", Mayo Clinic Proc., vol. 88, No. 8, Aug. 2013, pp. 782-785, Mayo Foundation for Medical Education and Research.

(56) References Cited

OTHER PUBLICATIONS

Ben-Amor, K., et al., "Genetic Diversity of Viable, Injured and Dead Fecal Bacteria Assessed by Fluorecence-Activated cell Sorting and 16S rRNA Gene Analysis", Applied and Environmental Microbiology, vol. 71, No. 8, Aug. 2005, pp. 4679-4689, American Society for Microbiology.

Bennett, P.S., et al., "What Nurses Need to Know About Fecal Microbiota Transplantation: Education, Assessment, and Care for Children and Young Adults", J. Pediatr Nurs., Feb. 7, 2014, doi: 10.1016/j.pedn.2014.01.013 (8 pgs).

Kump, P., et al., "Alteration of Intestinal Dysbiosis by Fecal Microbiota Transplantation Does not Induce Remission in Patients with Chronic Active Ulcerative Colitis", Inflamm Bowel Dis, 2013, pp. 1-11, Crohn's & Colitis Foundation of America, Inc.

Kunde, S., et al., "Safety, Tolerability and Clinical Response after Fecal Transplantation in Children and Young Adults with Ulcerative Colitis", JPGN, vol. 56, No. 6, Jun. 2013, pp. 596-601.

Landy, J., et al., "Review Article: Faecal Transplantation Therapy for Gastrointestinal Disease", Alimentary Pharmacology and Therapeutics, vol. 34, 2011, pp. 409-415, Blackwell Publishing Ltd.

Lee, C., et al., "The outcome and long-term follow-up of 94 patients with recurrent and refractory Clostridium difficile infection using single to multiple fecal microbiota transplantation via retention enema", Eur J. Clin Microbiol Infect Dis., Mar. 14, 2014 (4 pgs.).

Lichtman, J., et al., "Host-Centric Proteomics of Stool: A Novel Strategy Focused on Intestinal Responses to the Gut Microbiota", Aug. 27, 2013, pp. 1-27, The American Society of Biochemistry and Molecular Biology, Inc.

Lofland, D., et al., "Fecal Transplant for Recurrent Clostridium difficile Infection", Clin Lab Sci., 2013, 26(3):131-5.

Lo Vecchio, A., et al., "Fecal Microbiota Transplantation for Clostridium difficile Infection: Benefits and Barriers", Current Opinion Gastroenterology, vol. 30, 2013, pp. 1-7, Wolters Kluwer Health and Lippincott Williams & Wilkins.

Marcille, J., "Fecal Microbiota Transplantation for Treating Recurrent Clostridium difficile Infection", Managed Care, Jun. 2013, pp. 18-19.

Martin, J., et al., "Clostridium difficile: biological therapies", Curr Opin Infect Dis., Oct. 2013; 26(5):454-60.

Mattila, E., et al., "Fecal Transplantation, Though Colonoscopy, is Effective Therapy for Recurrent Clostridium Difficile Infection ", Gastroenterology, vol. 142, 2012, pp. 490-496, AGA Institute.

Mccune, V.L., et al., "Faecal transplantation for the treatment of Clostridium difficile infecton: a review", Int J Antimicrob Agents, Mar. 2014; 43(3):201-6.

Mellow, M.H., et al., "Colonscopic Fecal Bacteriotherapy in the Treatment of Recurrent Clostridium Difficile Infection—Results and Follow-up", OSMA Journal, Mar. 2011, pp. 89-91.

Moayyedi, P., et al., "Canadian Association of Gastroenterology position statement: Fecal microbiota transplant therapy", Can J Gastroeneterol Hepatol, vol. 28, No. 2, Feb. 2014 (3 pgs.).

Mole, B., "FDA gets to Grips with Faeces", Nature, vol. 498, Jun. 13, 2013, pp. 147-148, Macmillan Publishers Limited.

O'Horo, J.C., "Treatment of Recurrent Clostridium difficile Infection: A Systematic Review", Infection, vol. 42, 2014, pp. 43-59, Springer.

Olle, B., "Medicines for Microbiota", Nature Biotechnology, vol. 31, No. 4, Apr. 2013, pp. 309-315, Nature America, Inc.

Orenstein, R., et al., "Moving Fecal Microbiota Transplantation Into the Mainstream", Nutrition in Clinical Practice, vol. 28, No. 5, Oct. 2013, pp. 589-598, American Society for Parenteral and Enteral Nutrition.

Ott, S., et al., "In Vitro Alterations of Intestinal Bacterial Microbiota in Fecal Samples through Storage", Diagnostic Microbiology & Infectious Disease, vol. 50, 2004, pp. 237-245, Elsevier.

Ott, S., et al., "Quantification of Intestinal Bacterial Populations by Real-Time PCR with a Universal Primer Set and Minor Groove Binder Probes: a Global Approach to the Enteric Flora", Journal of Clinical Microbiology, vol. 42, No. 6, Jun. 2004, pp. 2566-2572, American Society for Microbiology.

Owens, C., et al., "Fecal Microbiota Transplantation and Donor Standardization", Trends in Microbiology, vol. 21, No. 9, Sep. 2013, pp. 443-445.

Pamer, E.G., "Fecal Microbiota Transplantation: Effectiveness, Complexities, and Lingering Concerns", 2014, pp. 1-5, Nature Publishing Group.

Patel, N., et al., "Fecal Microbiota Transplant for Recurrent Clostridium difficile Infection: Mayo Clinic in Arizona Experience", Mayo Clinic Proceedings, vol. 88, No. 8, Aug. 2013, pp. 799-805, Mayo Foundation for Medical Education and research.

Patel, L. N., et al., "Fecal Transplantation Therapy for Clostridium difficile—Associated Pouchitis", Int J Colorectal Dis, vol. 29, 2014, pp. 263-264, Springer.

Paterson, D., et al., "Putting Back the Bugs: Bacterial Treatment Relieves Chronic Diarrhea", The Medical Journal of Australia, vol. 160, Feb. 21, 1994, pp. 232-233.

Pathak, R., et al., "Treatment of Relapsing Clostridium difficile Infection using Fecal Microbiota Transplantation", Clinical and Experimental Gastroenterology, vol. 7, Dec. 27, 2013, pp. 1-7, DovePress.

Peterson, B., et al., "Bacterial Cell Surface Damage due to Centrifugal Compaction", Applied and Environmental Microbiology, vol. 78, No. 1, Jan. 2012, pp. 120-125.

Petrof, E.O., et al., "From Stool Transplants to Next-Generation Microbiota Therapeutics", Gastroenterology, Jan. 6, 2014, pp. 1-29.

Postgate, J.R., et al., "On the Survival of Frozen Bacteria", J. Gen. Microbiol., vol. 26, Feb. 9, 1961, pp. 367-378.

Roesch, L., et al., "Influence of Fecal Sample Storage on Bacterial Community Diversity", The Open Microbiology Journal, vol. 3, 2009, pp. 40-46.

Rohlke, F., et al., "Fecal microbiota transplantation in relapsing Colostridium difficile infection", Therap Adv Gastroenterol., Nov. 2012; 5(6):403-20.

Rubin, D., "Curbing our Enthusiasm for Fecal Transplantation in Ulcerative Colitis", The American Journal of Gastroenterology, vol. 108, 2013, pp. 1631-1633, nature publishing group.

Rubin, T.A., et al., "Fecal microbiome transplantation for recurrent Clostridium difficile infection: Report on a case series", Anaerobe 19 (2013) 22-26.

Russell, G., et al., "Fecal Bacteriotherapy for Relapsing Clostridium difficile Infection in a Child: A Proposed Treatment Protocol", Pediatrics, vol. 126, No. 1, Jul. 2010, pp. e239-e242, American Academy of Pediatrics.

Savani, M., et al., "Pilot-Scale Production and Viability Analysis of Freeze-Dried Probiotic Bacteria Using Different Protective Agents," Nutrients, vol. 2, pp. 330-339, 2010.

Schwan, A., et al., "Relapsing Clostridium Difficile Enterocolitis Cure by Rectal Infusions of Normal Feces", Scand J Infect Dis, vol. 16, 1984, pp. 211-215.

Schwartz, M., et al., "Norovirus Gastroenteritis After Fecal Microbiota Transplantation for Treatment of Clostridium Difficile Infection Despite Asymptomatic Donors and Lack of Sick Contacts", American Journal of Gastroenterology, vol. 108, Aug. 2013, pp. 1367-1368, American College of Gastroenterology.

Senior, K., "Faecal transplantation for recurrent C difficile diarrhoea", Lancet Infect Dis., Mar. 2013; 13(3):200-1.

Sha, S., et al., "Systematic review: faecal microbiota transplantation therapy for digestive and nondigestive disorders in adults and children", Aliment Pharmacol Ther, May 2014; 39(10):1003-32.

Silverman, M., et al., Success of Self-Administered Home Fecal Transplantation for Chronic Clostridium Difficile Infection, Clinical Gastroenterology and Hepatology, vol. 8, No. 5, 2010, pp. 471-473, AGA Institute.

Smith, M.B., et al., "Policy: How to regulate faecal transplants", Nature, Feb. 20, 2014; 506(7488):290-1.

Sofi, A., et al., "Physician outlook toward fecal microbiota transplantation in the treatment of Clostridium difficile infection", Am J Gastroenterol, Oct. 2013; 108(10):1661-2.

Solari, P., et al., "Tempered enthusiasm for Fecal transplantation", Clin Infect Dis, Apr. 23, 2014 (3 pgs.).

Song, Y., et al., "Microbiota Dynamics in Patients Treated with Fecal Microbiota Transplantation for Recurrent Clostridium difficile Infection", PLOS One, vol. 8, Issue 11, Nov. 2013, pp. 1-11.

(56) References Cited

OTHER PUBLICATIONS

Swift, H., "Preservation of Stock Cultures of Bacteria by Freezing and Drying", Jan. 1, 1921, pp. 1-7.
Damman, C., et al., "The Microbiome and Inflammatory Bowel Disease: Is There a Therapeutic Role for Fecal Microbiota Transplantation?", The American Journal of Gastroenterology, vol. 107, Oct. 2012, pp. 1452-1459, nature publishing group.
Dan, M., et al., "Comparison of Preservation Media and Freezing Conditions for Storage of Specimens of F0eces", J. Med Microbiol., vol. 28, 1989, pp. 151-154, The Pathological Society of Great Britain and Ireland.
Davidovics, Z.H., et al., "Medical Stool: The Future Treatment of Inflammatory Bowel Disease?", JPGN, vol. 56, No. 6, Jun. 2013, p. 583, Espghan and Naspghan.
De Leon, L.M., et al., "Transient Flare of Ulcerative Colitis after Fecal Microbiota Transplantation for Recurrent Clostridium difficile Infection", Clinical Gastroenterology and Hepatology, vol. 11, 2013, pp. 1036-1038, AGA Institute.
De Vrieze, J., "The Promise of Poop", Science, vol. 341, Aug. 30, 2013, pp. 954-957, AAAS.
Dubberke, E.R., et al., "Burden of Clostridium difficile on the Healthcare System", CID 2012:55 (Suppl 2), S88-S92.
Dubberke, E., "Clostridium Difficile Infection: The Scope of the Problem", Journal of Hospital Medicine, vol. 7, Supp. 3, Mar. 2012, S1-S4.
Dubberke, E.R., et al., "The Ecology and Pathobiology of Clostridium Difficile Infections: An Interdisciplinary Challenge", 2001, pp. 1-31.
Dutta, S.K., et al., "Efficacy of Combined Jejunal and Colonic Fecal Microbiota Transplantation for Recurrent Clostridium difficile Infection", Clinical Gastroenerology and Hepatology, 2013, pp. 1-19.
Ehlermann, P., et al., "Donor fecal transfer for recurrent Clostridium difficile-associated diarrhea in heart transplantation", The Journal of Heart and Lung Transplantation, vol. 33, No. 5, May 2014, pp. 551-553.
Eiseman, B., et al., "Fecal Enema as an Adjunct in the Treatment of Pseudomembranous Enterocolitis", Surgery, vol. 44, No. 5, Nov. 1958, pp. 854-859.
El-Matary, W., "Fecal Microbiots Transplantation: Long-Term Safety Issues", The American Journal of Gastroenterology, 2013, pp. 1537-1538, American College of Gastroenterology.
Floch, M., "Fecal Bacteriotherapy, Fecal Transplant and the Microbiome", J Clin Gastroenterol, vol. 44, No. 8, Sep. 2010, pp. 529-530, Lippincott Williams & Wilkins.
Flores, R., et al., "Assessment of the Human Faecal Microbiota: II. Reproducibility and Associations of 16s rRNA Pyrosequences", European Journal of Clinical Investigation, vol. 42, 2012, pp. 855-863.
Fox, J., "Fecal Transplants to Follow FDA Rules", Nature Biotechnology, vol. 31, No. 7, Jul. 2013, p. 583, Nature America, Inc.
Franks, A., et al., "Variations of Bacterial Populations in Human Feces Measured by Fluorecent in Situ Hybridization with Group-Specific 16S rRNA-Targeted Oligonucleotide Probes", Applied and Environmental Microbiology, vol. 64, No. 9, Sep. 1998, pp. 3336-3345, American Society for Microbiology.
Friedman-Moraco, R.J., et al., "Fecal Microbiota Transplantation for Refractory Clostridium difficile Colitis in Solid Organ Transplant Recipients", American Journal of Transplantation, vol. 14, 2014, pp. 477-480, The American Society of Transplantation and the American Society of Transplant Surgeons.
Gough, E., et al., "Systematic Review of Intestinal Microbiota Transplantation (Fecal Bacteriotherapy)for Recurrent Clostridium difficile Infection", Clinical Infectious Diseases, vol. 53, No. 10, Nov. 15, 2011, pp. 994-1002, Oxford University Press on behalf of the Infectious Diseases Society of America.
Guo, B., et al., "Systematic review: faecal transplantation for the treatment of Clostridium difficile-associated disease", Aliment Pharmacol. Ther. 2012; 35:865-875.
Hamilton, M., et al., "High-Throughput DNA Sequence Analysis Reveals a Stable Engraftment of Gut Microbiota Following Transplantation of Previously Frozen Fecal Bacteria", Gut Microbes, vol. 4, No. 2, Mar./Apr. 2013, pp. 125-135, Landes Bioscience.
Hamilton, M., et al., "Preservation of Stock Cultures of Bacteria by Freezing and Drying", The American Journal of Gastroenterology, vol. 107, May 2012, pp. 761-767, American College of Gastroenterology.
Hecht, G.A., et al., "What's the Value of an FDA IND for Fecal Microbiota Transplantation in Clostridium difficile Infection?", Clinical Gastroenterology and Hepatology, 2013, pp. 1-10.
Henning, T., "Polyethlene Glycols (PEGs) and the Pharmaceutical Industry", Fine, Specialty & Performance Chemicals, Jun. 2002, pp. 57-59.
Hubalek, Z., "Protectents Used in the Cryopreservation of Microorganisms", Cryobiology, vol. 46, 2003, pp. 225-229, Elsevier Science (USA).
Jiang, Z., et al., "Physician Attitudes Toward the use of Fecal Transplantation for Recurrent Clostridium difficile Infection in a Metropolitan Area", Clinical Infectious Diseases, vol. 56, Apr. 1, 2013, pp. 1059-1060, Oxford University Press on behalf of the Infectious Diseases Society of America.
Kahn, S., et al., "Colonoscopic Fecal Microbiota Transplant for Recurrent Clostridium difficile Infection in a Child", The American Journal of Gastroenterology, vol. 107, Dec. 2012, pp. 1930-1931, the American College of Gastroenterology.
Kahn, S., et al., "Fecal Bacteriotherapy for Ulcerative Colitis: Patients Are Ready, Are We?", Inflammatory Bowel Disease, vol. 18, No. 4, Apr. 2012, pp. 676-684.
Kao, D., et al., "Fecal Microbiota Transplantation Inducing Remission in Crohn's Colitis and the Associated Changes in Fecal Microbial Profile", J Clin Gastroenterol, 2014, PMID: 24667590 (4 pgs.).
Karadsheh, Z., et al., "Fecal Transplantationfor the Treatment of Recurrent Clostridium Difficile Infection", Northern American Journal of Medical Sciences, vol. 5, Issue 6, 2013, pp. 339-343.
Kassam, Z., et al., "Fecal Microbiotia Transplantation of Clostridium Difficile Infection: Systematic Review and Meta-Analysis", American Journal of Gastroenterol, vol. 108, No. 4, 2013, pp. 500-508.
Kassam, Z., et al., "Fecal Transplant Via Retention Enema for Refractory or Recurrent Clostridium Difficile Infection", Arch Intern Med, vol. 172, No. 2, Jan. 23, 2012, pp. 191-193, American Medical Association.
Kassam, Z., et al., "Navigating Long-Term Safety in Fecal Microbiota Transplantation", The American Journal of Gastroenterology, vol. 108, Sep. 2013, p. 1538.
Kellermayer, R., "Prospects and Challenges for Intestinal Microbiome Therapy in Pediatric Gastrointestinal Disorders", World Journal of Gastrointestinal Pathophysiology (WJGP), vol. 4, No. 4, Nov. 15, 2013, pp. 91-93, Baishideng Publishing Group Co., Limited.
Kelly, C., "FDA's Role in Regulating FMT is Imperative", AGA Perspectives Online, Dec. 20, 2013, pp. 1-2.
Kelly, C., et al., "A How to Guide: Investigational New Drug Application of Fecal Microbiota Transplantation", Clinical Gastroenterology and Hepatology, 2013, pp. 1-40.
Khoruts, A., et al., "Changes in the Composition of the Human Fecal Microbiome After Bacteriotherapy for Recurrent Clostridium Difficile Associated Diahrrea", J Clin Gastroenterol, vol. 44, No. 5, May/Jun. 2010, pp. 354-360, Lippincott Williams & Wilkins.
Khoruts, A.,et al., "Therapeutic Transplantation of the Distal Gut Microbiome", Nature Publishing Group, vol. 4, No. 1, Dec. 8, 2010, pp. 4-7.
Koboziev, I., et al., "Role of the Enteric Microbiota in Intestinal Homeostasis and Inflammation", Free Radical Biology and Medicine, 2013, pp. 1-38.
Konstantinov, S., et al., "Fecal Microbiota Transfer May Increase Irritable Bowel Syndrome and Inflammatory Bowel Diseases—Associated Bacteria", Gastroenterology, vol. 144, No. 4, Apr. 2013, pp. e19-e20.
Kuk, S., et al., "Stool Sample Storage Conditions for the Preservation of Giardia intestinalis DNA", Memorial Institute of Oswaldo Cruz, Rio de Janeiro, vol. 107, No. 8, Dec. 2012, pp. 965-968.
Berejnov, V., et al., "Effects of cryoprotectant concentration and cooling rate on vitrification of aqueous solutions," J. Appl. Cryst. (2006) 39, 244-251.

(56) References Cited

OTHER PUBLICATIONS

Hamilton et al., "Standardized Frozen Preparation for Transplantation of Fecal Microbiota for Recurrent Clostridium Difficile Infection," The American Journal of Gastroenterology, Jan. 31, 2012.
Mcfarland et al., "Recurrent Clostridium Difficile Disease: Epidemiology and Clinical Characteristics," Infection Control and Hospital Epidemiology, 20.01: 43-50, 1999.
Pray et al., "The Human Microbiome, Diet, and Health," Institute of Medicine of the National Academies, 2013.
Frantzen, M. et al., "Empirical Evaluation of Preservation Methods for Faecal DNA," Molecular Ecology, vol. 7, 1423-1428, 1998.
Segata, N. et al., "Composition of the Adult Digestive Tract Bacterial Microbiome Based on Seven Mouth Surfaces, Tonsils, Throat and Stool Samples," Genome Biology, vol. 13, 2012.
Taur, Y. et al., "Harnessing Microbiota to kill a pathogen," Nature Medicine, 20(3), 246-247, 2014.
Smith, M. et al., "How to regulate Faecal Transplants," Nature, vol. 506, 290-291, 2014.
Vaishnavi, C., "Fecal Microbiota Transplantation for Management of Clostridium Difficile Infection," Indian Society of Gastroenterology, vol. 33(a),301-307, 2014.
Ianiro, G. et al., "Fecal Microbiota Transplantation in Inflammatory Bowel Disease: Beyond the Excitement," Medicine, 93(19), 1-11, 2014.
Satokari, R. et al., "Simple Faecal Preparation and Efficacy of Frozen Inoculum in Faecal Microbiota Transplantation for Recurrent Clostridium Difficile Infection—an Observational Cohort Study," AP&T Alimentary Pharmacology and Therapeutics, vol. 41, 46-53, 2014.
Wang, Z. et al., "Intestinal Microbiota Pathogenesis and Fecal Microbiota Transplantation for Inflammatory Bowel Disease," World Journal of Gastroenterology, 20(40), 14805-14820, 2014.
Buffie, C. et al., "Precision Microbiome Reconstitution Restores Bile Acid Mediated Resistance to Clostridium Difficile," Nature, vol. 517, 2014.
Ratner, M., "Fecal Transplantation Poses Dilemma for FDA," Nature Biotechnology, 32(5), 401-402, 2014.
Russell, G. et al., "Fecal Transplant for Recurrent Clostridium Difficile Infection in Children With and Without Inflammatory Bowel Disease," Original Article: Gastroenterology, vol. 58, 588-592, 2014.
Shanahan, F. et al., "Manipulation of the Microbiota for Treatment of IBS and IBD—Challenges and Controversies," Gastroenterology, vol. 146, 1554-1563, 2014.
Shankar, V. et al., "Species and Genus Level Resolution Analysis of Gut Microbiota in Clostridium Difficile Patients Following Fecal Microbiota Transplantation," Microbiome, 2(13), 1-10, 2014.
Zacharioudakis, I. et al., "Clostridium Difficile Infection: an Undeniably Common Problem Among Hematopoietic Transplant Recipients," Springer, vol. 100, 514-515, 2014.
Varier, R. et al., "Cost-effectiveness Analysis of Treatment Strategies for Initial Clostridium Difficile Infection," Clinical Microbiology and Infection, 20(12), 1343-1351, 2014.
Hohmann, E. et al., "Case 25-2014: A 37-Year-Old Man with Ulcerative Colitis and Bloody Diarrhea," The New England Journal of Medicine, vol. 371,668-675, 2014.
Khoruts, A. et al., "Emergence of Fecal Microbiota Transplantation as an Approach to Repair Disrupted Microbial Guy Ecology," Elsevier, vol. 162, 77-81, 2014.
Mergenhagen, K. et al., "A Review of the Economics of Treating Clostridium Difficile Infection," PharmacoEconomics, vol. 32, 639-650, 2014.
Zainah, H. et al., "Intestinal Microbiota Transplantation, a Simple and Effective Treatment for Severe and Refractory Clostridium Difficile Infection," Springer Science and Business Media, vol. 60, 181-185, 2015.
Duke, P. et al., "Recurrent Clostridium Difficile Infection Treated with Home Fecal Transplantation: a Case Report," Journal of Medical Case Reports, 8(393),1-4, 2014.
Kassam, Z. et al., "Review of the Emerging Treatment of Clostridium Difficile Infection with Decal Microbiota Transplantation and Insights into Future Challenges," Clin Lab Med, vol. 34, 787-798, 2014.
Khoruts, A. et al., "Development of Fecal Microbiota Transplantation Suitable for Mainstream Medicine," Clinical Gastroenterology and Hepatology, vol. 13, 246-250, 2014.
Mandalia, A. et al., "Diverticulitis after Fecal Microbiota Transplant for C. Difficile Infection," The American Journal of Gastroenterology, vol. 109, 1956-1957, 2014.
Pinn, DM. et al., "Is Fecal Microbiota Transplantation an Effective Treatment for Patients with Functional Gastrointestinal Disorders?" Neurogastroenterology & Motility, vol. 27, 19-29, 2014.
Baines, S.D. et al., "SMT19969 as a Treatment for Clostridium Difficile Infection: an Assessment of Antimicrobial Activity Using Conventional Susceptibility Testing and an in Vitro Gut Model," Journal of Antimicrobial Chemotherapy, vol. 70, 182-189, 2015.
Patel, R., "Vancomycin-Resistant Enterococcal Bacteremia Pharmacotherapy," Annals of Pharmacotherapy, vol. 49(1): 69-85, 2015.
Borody, TJ. et al., "Clostridium Difficile Complicating Inflammatory Bowel Disease: Pre- and Post-Treatment Findings," AGA Abstracts, pp. A-361, 2008.
Brandt, LJ. et al., "Fecal Microbiota Transplantation for Recurrent Clostridium Difficile Infection," J Clin Gastroenterol, vol. 45, S159-S167, 2011.
Drekonja, D. et al., "Comparative Effectiveness of Clostridium Difficile Treatments," Annals of Internal Medicine, vol. 155(12): 839-W269, 2011.
Duplessis, C. et al., "Efficacious Outcome Employing Fecal Bacteriotherapy in Sever Crohn's Colitis Complicated by Refractory Clostridium Difficile Infection," Infectio, vol. 40, 469-472, 2012.
Gallegos-Orozco, JF. et al., "Successful Colonoscopic Fecal Transplant for Severe Acute Clostridium Difficile Pseudomembranous Colitis," Rev Gastroenteral Mex, vol. 77(1):39-42, 2012.
Garborg, K. et al., "Results of Faecal Instillation Therapy for Recurrent Clostridium Difficile-Associated Diarrhoea," Journal of Infectious Diseases, vol. 42, 857-861, 2010.
Venugopal, A. et al., "Current State of Clostridium Difficile Treatment Options," CID, vol. 55, S71-S76, 2012.
Watson, J. et al., "First Reported Complication of Fecal Microbiota Transplant: Ulcerative Colitis Flare after FMT for Relapsing Clostridium Difficile Infection," AGA Abstracts, p. S540, 2012.
Yoon, S. et al., "Treatment of Refractory/Recurrent C. Difficile-Associated Disease by Donated Stool Transplanted Via Colonoscopy," J Clin Gastroenterol, vol. 44(8): 562-566, 2010.
Moore, T. et al., "Fecal Microbiota Transplantation: A Practice Update for the Infectious Disease Specialist," HealthCare Epidemiology, vol. 58, 541-545, 2014.
Hedge, DD. et al., "New Advances in the Treatment of Clostridium Difficile Infection," Therapeutics and Clinical Risk Management, vol. 4(5): 949-964, 2008.
Kelly, CR. et al., "Fecal Microbiota Transplantation for Relapsing Clostridium Difficile Infection in 26 Patients: Methodology and Results," J Clin Gastroenterol, vol. 46(2): 145-149, 2012.
Macconnachie, A.A. et al., "Faecal Transplant for Recurrent Clostridium Difficile-Associated Diarrhoea: a UK Case Series," QJ Med, vol. 102, 781-784, 2009.
Persky, S. et al., "Treatment of Recurrent Clostridium Difficile-Associated Diarrhea by Administration of donated stool Directly through a Colonoscopy," The American Journal of Gastroenterology, vol. 95(11): 3283-3285, 2000.
Postigo, R. et al., "Colonoscopic Versus Nasogastric Fecal Transplantation for the treatment of Clostridium Difficile Infection: a Review and Pooled Analysis," Infection, vol. 40, 643-648, 2012.
Rohlke, F. et al., "Fecal Flora Reconstitution for Recurrent Clostridium Difficile Infection: Results and Methodology," J Clin Gastroenterol, vol. 44(8): 567-570, 2010.
Anderson, J. et al., "Systematic Review: Faecal Microbiota Transplantation in the Management of inflammatory bowel Disease," Aliment Pharmacol Ther, vol. 36, 503-516, 2012.
Borody, T.J. et al., "Fecal Microbiota Transplantation and Emerging Application," Gastroenterol Clin N Am, vol. 41, 781-803, 2011.

(56) References Cited

OTHER PUBLICATIONS

Borody, T.J. et al., "Is Crohn's Disease Ready for Fecal Microbiota Transplantation?" J Clin Gastroenterol, vol. 48(7): 582-583, 2014.
Colman, R. et al., "Fecal Microbiota Transplantation as Therapy for Inflammatory Bowel Disease: a Systematic review and meta-analysis," Elsevier, vol. 8, 1569-1581, 2014.
Cui, B. et al., "Fecal Microbiota Transplantation through Mid-Gut for Refractory Crohn's Disease: Safety, Feasibility, and Efficacy Trial Results," Journal of Gastroenterology and Hepatology, vol. 30, 51-58, 2014.
Cox, C.S., "Bacterial Survival in Suspension in Polyethylene Glycol Solutions," J. Gen. Microbiol. 45, 275-281 (1966).
Satokari, R., et al., "Simple faecal preparation and efficacy of frozen inoculum in faecal microbiota transplantation for recurrent Clostridium difficile infection—an observational cohort study," Aliment Pharmacol Ther 2015; 41: 46-53.
De Vos, W., "Fame and Future of Faecal Transplantations—Developing Next-Generation Therapies with Synthetic Microbiomes," Microbial Biotechnology, vol. 6(4): 316-325, 2013.
Gevers, D. et al., "The Treatment-Naive Microbiome in new-onset Crohn's Disease," Cell Host & Microbe, vol. 15, 382-392, 2014.
Hold, G. et al., "Role of the gut Microbiota in Inflammatory Bowel Disease Pathogenesis: What have we learnt in the past 10 years?" World Journal of Gastroenterology, vol. 20(5): 1192-1210, 2014.
Hollister, E. et al., "Compositional and Functional Features of the Gastrointestinal Microbiome and their Effects on Human Health," Gastroenterology, vol. 146, 1449-1458, 2014.
Ianiro, G. et al., "Letter: Faecal Microbiota Transplantation—not a one-size-fits-all approach," Aliment Pharmacol Ther, vol. 40, 117-122, 2014.
Kostic, A. et al., "The Microbiome and Inflammatory Bowel Disease: Current Status and the Future Ahead," Gastroenterology, vol. 146, 1489-1499, 2014.
Liang, J. et al., "Role of the Intestinal Microbiota and Fecal Transplantation in Inflammatory Bowel Diseases," Journal of Digestive Diseases, vol. 15, 641-646, 2014.
Morgan, X. et al., "Dysfunction of the Intestinal Microbiome in Inflammatory Bowel Disease and Treatment," Genome Biology, vol. 13, 1-18, 2012.
Owyang, C. et al., "The Gut Microbiome in Health and Disease," Gastroenterology, vol. 146, 1433-1436, 2014.
Hofer, U., "Bacterial Imbalance in Crohn's Disease," Nature Reviews Microbiology, vol. 12, 2014.
Rogers, G. et al., "Challenges and Opportunities for Faecal Microbiota Transplantation Therapy," Epidemiol. Infect, vol. 141, 2235-2242, 2014.
Scaldaferri, F. et al., "Gut Microbial Flora, Prebiotics, and Probiotics in IBD: Their Current Usage and Utility," BioMed Research International, pp. 1-10, 2013.
Singh, R. et al., "The Potential Beneficial Role of Faecal Microbiota Transplantation in Diseases other than Clostridium Difficile Infection," Clin Microbiol Infect, vol. 20, 1119-1125, 2014.
Smits, L. et al., "Therapeutic Potential of Fecal Microbiota Transplantation," Gastroenterology, vol. 145, 946-953, 2013.
Xu, M. et al., "Fecal Microbiota Transplantation Broadening its application beyond Intestinal Orders," World J Gastroenterol, vol. 21(1): 102-111, 2015.
Bae, S. et al., "Discrimination of Viable and Dead Fecal Bacteroidales Bacteria by Quantitative PCR with Propidium Monoazide," Applied and Environmental Microbiology, vol. 75(9): 2940-2944, 2001.
Chakravorty, S. et al., "A Detailed Analysis of 16s Ribosomal RNA Gene Segments for the Diagnosis of Pathogenic Bacteria," Journal of Microbiological Methods, vol. 69, 330-339, 2007.
Cammarota, G. et al., "The Involvment of Gut Microbiota in Inflammatory Bowel Disease Pathogensis: Potential for Therapy," Pharmacology and Therapeutics, vol. 149, 191-212, 2015.
Cammarota, G. et al., "Randomised Clinical Trial: Faecal Microbiota Transplantation by Colonoscopy vs. Vancomycin for the Treatment of recurrent Clostridium Difficile Infectino," Aliment Pharmacol Ther, vol. 41, 835-843, 2015.

Di Bella, S. et al., "Fecal Microbiota Transplantation (FMT) for Clostridium Difficile Infection: Focus on Immunocompromised Patients," Journal of Infection and Chemotherapy, vol. 21, 230-237, 2015.
Gregory, J. et al., "Transmission of Atherosclerosis Susceptibility with Gut Microbial Transplantation," Journal of Biological Chemistry, vol. 290(9): 5647-5660, 2015.
Keller, J.J. et al., "Treatment of Recurrent and Severe Clostridium Difficile Infection," The Annual Review of Medicine, vol. 66,373-86, 2015.
Ray, A. et al., "Fecal Microbiota Transplantation for Clostridium difficile Infection: The Ochsner Experience," The Ochsner Journal, vol. 14, 538-544, 2014.
Vyas, D. et al., "Fecal Transplant Policy and Legislation," World Journal of Gastroenterology, vol. 21(1):6-11, 2015.
Kramer, M. et al., "Quantification of live and dead probiotic bacteria in lyophilised product by real-time PCR and by Flow Cytometry," Appl. Microbiol Biotechnol, vol. 84, 1137-1147, 2009.
Taskin, B. et al., "Selective Quantification of Viable *Escherichia Coli* Bacteria in Biosolids by Quantitative PCR with Propidium Monoazide Modification," Applied and Environmental Microbiology, vol. 77(13): 4329-4335, 2011.
Surawicz, C. et al. "Guidelines for Diagnosis, Treatment and Prevention of Clostridium Difficile Infections," The American Journal of Gastroenterology. vol. 108:478-498, 2013.
Swaminath, A. et al. ,"The Power of Poop: Patients Getting Ahead of Their Doctors Using Self-Administered Fecal Transplants," The American Journal of Gastroenterology, vol. 109, 777-778, 2014.
Pinn, "Is Fecal Microbiota Transplantation the Answer for Irritable Bowel Syndrome? A Single-Center Experience," The American Journal of Gastroenterology, vol. 109, 1831-1832, 2014.
Gwoen, T. et al., "A Case of Toxic Megacolon Caused by Clostridium Difficile Infection and Treated with Fecal MIcrobiota Transplantation," Gut and Live, vol. 9(2):247-250, 2015.
Matuchansky, C., "Fecal Microbiota Transplantation: The Case of the Immunocompromised Patients," The American Journal of Medicine, p. 1, 2015.
Dennis, M. et al., "Low Awareness but Positive Attitude toward Fecal Transplantation in Ontario Physicians," Can J Infect Dis Med Microbiol, vol. 26(1):30-32, 2015.
Tauxe, We. et al., "Fecal Microbiota Transplant Protocol for Clostridium Difficile Infection," Lab Medicine, vol. 46(1):e19-e23, 2015.
Wang, J. et al., "Pediatric Severe Pseudomembranous enteritis treated with fecal Microbiota Transplantation in a 13-month-old infant," Biomedical Reports, vol. 3,173-175, 2015.
Boyle, M. et al., "Fecal Microbiota Transplant to treat Recurrent Clostridium difficile infections," Critical Care Nurse, vol. 35(2):51-64, 2015.
Brechmann, T. et al., "Complicated Fecal Microbiota Transplantation in a Tetraplegic Patient with Severe Clostridium Difficile Infection," World Journal of Gastroenterology, vol. 21(12):3736-3740, 2015.
Rossen, N. et al., "Findings from a Randomized Controlled Trial of Fecal Transplantation for Patients with Ulcerative Colitis," Gastroenterology, vol. 149, 110-118, 2015.
Ohtake, S. et al., "Trehalose: Current Use and Future Applications," Journal of Pharmaceutical Sciences, vol. 100(6): 2020-2053, 2011.
Tian, H. et al., "Freeze-dried Capsulized Fecal Microbiota Transplantation for Relapsing Clostridium Difficile Infection," Journal Clinical Gastroenterol, vol. 49(6):537-538, 2015.
Crum-Cianflone, N.F. et al., "Fecal Microbiota Transplantation and the Successful Resolution of MDRO Colonization," Journal of Clinical Microbiology, vol. 53(6):1-4, 2015.
Hirsch, B.E. et al., "Effectiveness of fecal-derived Microbiota Transfer using Orally Administered capsules for recurrent Clostridium Difficile Infection," BMC Infectious Diseases, vol. 15(191):1-9, 2015.
Kellermayer, R. et al., "Serial Fecal Microbiota Transplantation Alters Mucosal Gene Expression in Pediatric Ulcerative Colitis," The American Journal of Gastroenterology, vol. 110, 604-606, 2015.

(56) References Cited

OTHER PUBLICATIONS

Moayyedi, P. et al., "Fecal Microbiota Transplantation Induces Remission in Patients with Active Ulcerative Colitis in a Randomized, Controlled Trial," Gastroenterology, vol. 149, 102-109, 2015.
Vickers, R. et al., "A Randomised Phase 1 Study to Investigate Safety, Pharmacokinetics and Impact on Gut Microbiota Following Single and Multiple oral doses in healthy make subjects of SMT19969, Novel Agent for CLostridium Difficile Infections," BMC Infectious Diseases, vol. 15(91):1-10, 2015.
Weil, A.A. et al., "Fecal Microbiota Transplant:Benefits and Risks," Editorial Commentary, pp. 1-2, 2015.
Mittal, C. et al., "Fecal Microbiota Transplant For Recurrent Clostridium Difficile Infection after Peripheral Autologous Stem cell Transplant for Diffuse Large B-Cell Lymphoma," Bone Marrow Transplantation, vol. 50, 1010, 2015.
Drekonja, D. et al., "Fecal Microbiota Transplantation for Clostridium Difficile Infection: A Systematic Review," Annals of Internal Medicine, vol. 162(9):630-639, 2015.
Costello, S.P. et al., "Fecal Microbiota Transplant for Clostridium Difficile Colitis-Induced Toxic Megacolon," The American Journal of Gastroenterology, vol. 110, 775-777, 2015.
Kump, P.K. et al., "Fecal Microbiota Transplantation—the Austrian Approach," Clinical Microbiology and Infection, vol. 20, 1106-1111, 2014.
Lagier, J. et al., "Dramatic Reduction in Clostridium Difficile Ribotype 027-associated mortality with early fecal Transplantation by the Nasogastric Route: A preliminary Report," European Journal of Clinical Microbiology and Infectious Diseases, vol. 34, 1597-1601, 2015.
Cox et al., "Altering the Intestinal Microbiota during a Critical Developmental Window has Lasting Metabolic Consequences," Cell, vol. 158, pp. 705-721, 2014.
Crum-Cianflone et al., "Fecal Microbiota Transplantation and the Successful Resolution of MDRO Colonization," Journal of Clinical Microbiology, pp. 1-15, 2015.
De Vos et al., "Fame and Future of Faecal Transplantations—Developing next-generation Therapies with Syntheitc Microbiomes," Microbial Biotechnology, vol. 6(4): 316-325, 2013.
Dubberke et al., "Attributable Inpatient Costs of Recurrent Clostridium Difficile Infections," Chicago Journals, vol. 35(11): 1400-1407, 2014.
Faust et al., "Treatment of Recurrent Pseudomembranous Colitis (RPMC) with Stool Transplantation (ST): Report of Six (6) Cases," Search CDDW Abstracts, pp. 1-1, 2002.
Kump et al., "Fecal Microbiota Transplantation—The Austrian Approach," doi: 10.1111/1469-0691.12801, 2014.
Moayyedi et al., "Fecal Microbiota Transplantation Induces Remission in Patients with Active Ulcerative Colitis in a Randomized, Controlled Trial," Gastroenterology, pp. 1-45, 2015.
Rossen et al., "Findings from a Randomized Controlled Trial of Fecal Transplantation for Patients with Ulcerative Colitis," Gastroenterology, doi: 10 1053/j.gastro.2015.03.045, pp. 1-48, 2015.
Seekatz et al., "Recovery of the Gut Microbiome Following Fecal Microbiota Transplantation," mBio, vol. 5(3): 1-9, 2014.
Louie, T. J. et al., "Differences of the Fecal Microflora with Clostridium Difficile Therapies," Microbial Flora in CDI Therapy, vol. 60, S91-S97, 2015.
Aratari et al., "Fecal Microbiota Transplantation for Recurrent C. Difficile Infection in a Patient with Chronic Refractory Ulcerative Colitis," Journal of Crohn's and Colitis, pp. 1-1, 2015.
Borody et al., "Clostridium Difficile Complicating Inflammatory Bowel Disease: Cure after Fecal Bacteriotherapy," FMT Studies and Reviews, pp. 1-1, 2008.
Borody et al., "Faecal Bacteriotherapy (FB) for Chronic C. Difficile (Cd) Syndromes," Journal of Gastroenterology and Hepatology, 18, B8, 2003.
Zhang et al., "Should We Standardize the 1,700-year-old Fecal Microbiota Transplantation?" The American Journal of Gastroenterology, vol. 251, 1755, 2012.
Faust et al., "Treatment of Recurrent Pseudomembranous Colitis (RPMC) with Stool Transplantation (ST): Report of six Cases," Search CDDW Abstracts, pp. 1-1, 2012.
Guo et al., "Fecal Transplantation for the Treatment of Clostridium Difficile-Associated Disease and/or Ulcerative Colitis," Institute of Health Economics, pp. 1-69, 2010.
Hellemans et al., "Fecal Transplantation for Recurrent Clostridium Difficile Colitis, an Underused Treatment Modality," Acta Gastro-Enterologica Belgica, vol. IXXII, 269-270, 2009.
Kasper et al., "Recent Advances and Further Challenges in Lyophilization," European Journal of Pharmaceutics and Biopharmaceutics, vol. 85,162-169, 2013.
Louie et al., "Home-Based Fecal FLora Infusion to Arrest Multiply-Recurrent Clostridium Difficile Infection (CDI)," Online Abstract Submission and Invitation System, pp. 1-1, 2008.
Martín et al., "Microencapsulation of Bacteria: A review of different Technologies and their impact on the Probiotic affects," Innovative Food Science and Emerging Technologies, vol. 27,15-25, 2015.
Stollman et al., "Frozen Encapsulated Stool in Recurrent Clostridium Difficile: Exploring the Role of Pills in the Treatment Hierarchy of Fecal Microbiota Transplant Nonresponder," The American Journal of Gastroenterology, vol. 110,600-601, 2015.
Vandenplas et al., "Fecal Microbiota Transplantation: just a fancy trend?" Journal of Pediatric Gastroenterology and Nutrition, pp. 1-15, 2015.
Varier et al., "Cost-Effectiveness Analysis of Fecal Microbiota Transplantation for Recurrent Clostridium Difficile Infection," Infection Control and Hospital Epidemiology, vol. 36,438-444, 2015.
Wettstein et al., "Fecal Bacteriotherapy—an effective Treatment for Relapsing Symptomatic Clostridium Difficile Infection," United European Gastroenterology Federation, pp. 1-1, 2007.
Wilcox., "Early Experience with a Fecal Bacteriotherapy (FB) Program for Recurrent and C-Difficile Infection (CDI)," AGA Abstracts, pp. S-361, 2011.
Cui et al., "Fecal Microbiota Transplantation through mid-gut for refractory Crohn's disease:safety,feasibility, and efficacy trial results," Journal of Gastroenterology and Hepatology, vol. 30,51-53, 2015.
Hamzelou, "The DIY Gut-bug swap," New Scientist, pp. 10-11, 2014.
Rao et al., "Fecal Microbiota Transplantation for the Management of Clostridium difficile Infection," Infect Dis Clin N Am 29 (2015) 109-122.
Arthur, J.; Jobin, C., Cancer, "The struggle within: microbial influences on colorectal cancer", Inflamm Bowel Dis. Jan. 2011 ; 17(1): 396-409.
Tedeschi, R., et al., "Collection and Preservation of Microorganisms", Methods in Molecular Biology, vol. 675, 2011, pp. 313-326, Springer Science + Business Media, LLC.
Tottey, W., et al., "The Human Gut Chip "HuGChip", an Explorative Phylogenic Microarray for Determining Gut Microbiome Diversity at Family Level", PLOS One, vol. 8, Issue 5, May 2013, pp. 1-12.
Tvede, M., et al., "Bacteriotherapy for Chronic Relapsing Clostridium Difficile Diarrhea in Six Patients", The Lancet, May 27, 1989, pp. 1156-1160.
Udayappan, S.D., et al., "Intestinal microbiota and fecal transplantation as treatment modality for insulin resistance and type 2 diabetes mellitus", Clin Exp Immunol., Feb. 15, 2014 (17 pgs.).
Vaishnavi, C., "Fecal microbiota transplantation for management of Clostridium difficile infection", Indian J Gastroenterol, Apr. 20, 2014 (7 pgs.).
Van den Abbeele, P., et al., "Prebiotics, Faecal Transplants and Microbial Network Units to Stimulate Biodiversity of the Human Gut Microbiome", Microbial Biotechnology, vol. 6, No. 4, 2013, pp. 335-340, John Wiley & Sons Ltd and Society for Applied Microbiology.
Van Nood, E., et al., "Duodenal Infusion of Donor Feces for Recurrent Clostridium Difficile", The New England Journal of Medicine, vol. 368, No. 5, Jan. 31, 2013, pp. 407-415, Massachusetts Medical Society.
Van Nood, E., et al., "Fecal Microbiota Transplantation: Facts and Controversies", Current Opinion Gastroenterology, vol. 30, 2014, pp. 1-6, Lippincott Williams & Wilkins.

(56) References Cited

OTHER PUBLICATIONS

Van Nood, E., et al., "Struggling with Recurrent Clostridium Difficile Infections: Is Donor Faeces the Solution?", Eurosurveillance, vol. 14, Issue 34, Aug. 27, 2009, pp. 1-6.
Vandenplas, Y., et al., "Fecal Microbial Transplantation in a One-Year-Old Girl with Early Onset Colitis—Caution Advised", J Pediatr Gastroenterol Nutr., Jan. 2, 2014 (11 pgs.).
Vrieze, A., et al., "Fecal Transplant: A Safe and Sustainable Clinical Therapy for Restoring Intestinal Microbial Balance in Human Disease?", Best Practice & Research Clinical Gastroenterology, vol. 27, 2013, pp. 127-137, Elsevier Ltd.
Vrieze, A., et al., "Transfer of Intestinal Microbiota from Lean Donors Increases Insulin Sensitivity in Individuals with Metabolic Syndrome", Gastroenterology, vol. 143, 2012, pp. 913-916, AGA Institute.
Vyas, D., et al., "Stool therapy May Become a Preferred Treatment of Recurrent Clostridium Difficile?", World Journal of Gastroenterology, vol. 19, Issue 29, Aug. 7, 2013, pp. 4635-4637, Baishideng.
Wasfy, M., et al., "Comparison of Preservation Media for Storage of Stool Samples", Journal of Clinical Microbiology, Aug. 1995, vol. 33, No. 8, pp. 2176-2178.
Weingarden, A., et al., "Microbiota Transplantation Restores Normal Fecal Bile Acid Composition in Recurrent Clostridium difficile Infection", Am J Physiol Gastrointest Liver Physiol, Nov. 27, 2013, pp. 1-30, American Physiology Society.
Wenfeng, S., et al., "Appraising Freeze-Drying for Storage of Bacteria and Their Ready Access in a Rapid Toxicity Assessment Assay", Appl Microbiol Biotechnol, 2013, pp. 1-10, Springer.
Wu, G.D., et al., "Analysis of the Human Gut Microbiome and Association with Disease", Clinical Gastroenterology and Hepatology, vol. 11, 2013, pp. 774-777, AGA Institute.
Youngster, I., et al., "Fecal Microbiota Transplant for Relapsing Clostridium difficile Infection Using a Frozen Inoculum From Unrelated Donors: A Randomized, Open-Label, Controlled Pilot Study", Clin Infect Dis., Apr. 2014; 58(11):1515-22.
Youngster, I., et al., "Supplementary Appendix: Fecal Microbiota Transplant for Relapsing Clostridium difficile Infection Using a Frozen Inoculum From Unrelated Donors: A Randomized, Open-Label, Controlled Pilot Study", Clin Infect Dis., Apr. 2014 (6 pgs.).
Zainah, H., et al., "Fecal Bacteriotherapy: A Case Report in an Immunossuppressed Patient with Ulcerative Colitis and Recurrent Clostridium difficile Infection", Case Reports in Infectious Diseases, 2012, pp. 1-2, Hindawi Publishing Corporation.
Zhang, F., et al., "Fecal Microbiota Transplantation for Severe Enterocolonic Fistulizing Crohn's Disease", World Journal of Gastroenterology, vol. 19, No. 42, Nov. 7, 2013, pp. 7213-7216, Baishideng Publishing Group Co., Limited.
Zhao, G., et al., "Effect of Protective Agents, Freezing Temperature, Rehydration Media on Viability of Malolactic Bacteria Subjected to Freeze-Drying", Journal of Applied Microbiology, vol. 99, 2005, pp. 333-338, The Society for Applied Microbiology.

\* cited by examiner

MICROBIOTA RESTORATION THERAPY (MRT) COMPOSITIONS AND METHODS OF MANUFACTURE

CROSS-REFERENCE TO RELATED APPLICATIONS

This application is a continuation of U.S. application Ser. No. 15/827,732, filed Nov. 30, 2017, which is a continuation of U.S. application Ser. No. 15/178,176, filed Jun. 9, 2016, now U.S. Pat. No. 10,226,431, which claims priority under 35 U.S.C. § 119 to U.S. Provisional Application Ser. No. 62/173,182, filed Jun. 9, 2015 and U.S. Provisional Application Ser. No. 62/247,825, filed Oct. 29, 2015, the entirety of which are incorporated herein by reference.

FIELD

The present disclosure pertains to compositions and methods for treating patients.

BACKGROUND

A wide variety of compositions and methods have been developed for treating diseases and/or conditions of the digestive track. Of the known compositions and methods, each has certain advantages and disadvantages. There is an ongoing need to provide alternative compositions and methods for treating diseases and/or conditions of the digestive track.

BRIEF SUMMARY

This disclosure provides design, material, manufacturing method, and use alternatives for compositions and methods for treating patients. An example method for manufacturing an oral microbiota restoration therapy (MRT) composition is disclosed. The method comprises:
collecting a stool sample;
purifying the stool sample to form a purified sample;
stabilizing the purified sample to form a stabilized sample;
converting the stabilized sample to a solid;
adding one or more additives and/or excipients to the solid to form a treatment composition; and
encapsulating the treatment composition.

An example method for manufacturing an oral microbiota restoration therapy (MRT) composition is disclosed. The method comprises:
collecting a stool sample;
purifying the stool sample to form a purified intermediate, wherein purifying the stool sample comprises:
adding a diluent to the stool sample;
mixing the stool sample and diluent to form a mixture;
filtering the mixture;
transferring a filtrate from the filtering step to a centrifuge tube; and
centrifuging the filtrate to arrive at the purified intermediate;
lyophilizing the purified intermediate to form a plurality lyophilized pellets; and
encapsulating the plurality of lyophilized pellets in one or more capsules.

Alternatively or additionally to any of the embodiments above, filtering the mixture comprises filtering the mixture to obtain a sample having particles in the range of 50 to 70 micrometers (μm).

Alternatively or additionally to any of the embodiments above, centrifuging the filtrate comprises centrifuging the filtrate at a rate such that the centrifugal force is in the range of about 8-12,000 g for in the range of 15 to 45 minutes.

Alternatively or additionally to any of the embodiments above, lyophilizing the purified intermediate comprises the steps of:
mixing the purified intermediate with a lyophilization excipient to form a lyophilization intermediate;
placing the lyophilization intermediate into a plate having a plurality of wells;
lowering a temperature of the lyophilization intermediate to a temperature in the range of −40 to −45° C.;
applying a vacuum to the lyophilization intermediate and raising the temperature of the lyophilization intermediate to approximately 0° C.;
initializing a secondary drying step and raising the temperature of the lyophilization intermediate to approximately 25° C.;
releasing the vacuum; and
removing a plurality of lyophilized pellets from the plate.

Alternatively or additionally to any of the embodiments above, the lyophilization excipient comprises at least 2.3% PEG 3350, 1% glycerin, 10% trehalose, and 10% sucrose.

Alternatively or additionally to any of the embodiments above, the one or more capsules comprise hypromellose capsule.

Alternatively or additionally to any of the embodiments above, further comprising banding the capsules.

Alternatively or additionally to any of the embodiments above, the banding material comprises hypromellose, an anionic copolymer based on methacrylic acid and methyl methacrylate, hypromellose phthalate, or hypromellose acetate succinate.

A method for manufacturing an oral microbiota restoration therapy (MRT) composition is disclosed. The method comprises:
adding a diluent to a purified stool sample, the purified stool sample comprising stool and a solution of 2.3% cryoprotectant and 0.9% sodium chloride solution;
mixing the stool sample and diluent to form a mixture;
filtering the mixture;
transferring a filtrate from the filtering step to a centrifuge tube; and
centrifuging the filtrate to arrive at the purified intermediate;
lyophilizing the purified intermediate to form a plurality lyophilized pellets; and
encapsulating the plurality of lyophilized pellets in one or more capsules.

Alternatively or additionally to any of the embodiments above, filtering the mixture comprises filtering the mixture to obtain a sample having particles in the range of 50 to 70 micrometers (μm).

Alternatively or additionally to any of the embodiments above, centrifuging the filtrate comprises centrifuging the filtrate at a rate such that the centrifugal force is in the range of about 8-12,000 g for in the range of 15 to 45 minutes.

Alternatively or additionally to any of the embodiments above, lyophilizing the purified intermediate comprises the steps of:
mixing the purified intermediate with a lyophilization excipient to form a lyophilization intermediate;
placing the lyophilization intermediate into a plate having a plurality of wells;
lowering a temperature of the lyophilization intermediate to a temperature in the range of −40 to −45° C.;

applying a vacuum to the lyophilization intermediate and raising the temperature of the lyophilization intermediate to approximately 0° C.;

initializing a secondary drying step and raising the temperature of the lyophilization intermediate to approximately 25° C.;

releasing the vacuum; and removing a plurality of lyophilized pellets from the plate.

Alternatively or additionally to any of the embodiments above, the lyophilization excipient comprises at least 2.3% PEG 3350, 1% glycerin, 10% trehalose, and 10% sucrose.

Alternatively or additionally to any of the embodiments above, the one or more capsules comprise hypromellose capsule.

Alternatively or additionally to any of the embodiments above, further comprising banding the capsules.

Alternatively or additionally to any of the embodiments above, the banding material comprises hypromellose, an anionic copolymer based on methacrylic acid and methyl methacrylate, hypromellose phthalate, or hypromellose acetate succinate.

Alternatively or additionally to any of the embodiments above, further comprising packaging the encapsulated lyophilized pellets into packets in individual dosage quantities.

Alternatively or additionally to any of the embodiments above, the packets comprises metallized polyester/polyethylene bonded film.

Alternatively or additionally to any of the embodiments above, further comprising placing the packets into one or more child-resistant containers.

Alternatively or additionally to any of the embodiments above, further comprising packaging the encapsulated lyophilized pellets into packets in individual dosage quantities.

Alternatively or additionally to any of the embodiments above, the packets comprises metallized polyester/polyethylene bonded film.

Alternatively or additionally to any of the embodiments above, further comprising placing the packets into one or more child-resistant containers.

The above summary of some embodiments is not intended to describe each disclosed embodiment or every implementation of the present disclosure. The Figures and Detailed Description which follow more particularly exemplify these embodiments.

BRIEF DESCRIPTION OF THE DRAWINGS

The disclosure may be more completely understood in consideration of the following detailed description of various embodiments of the disclosure in connection with the accompanying drawings, in which.

Figure 1:
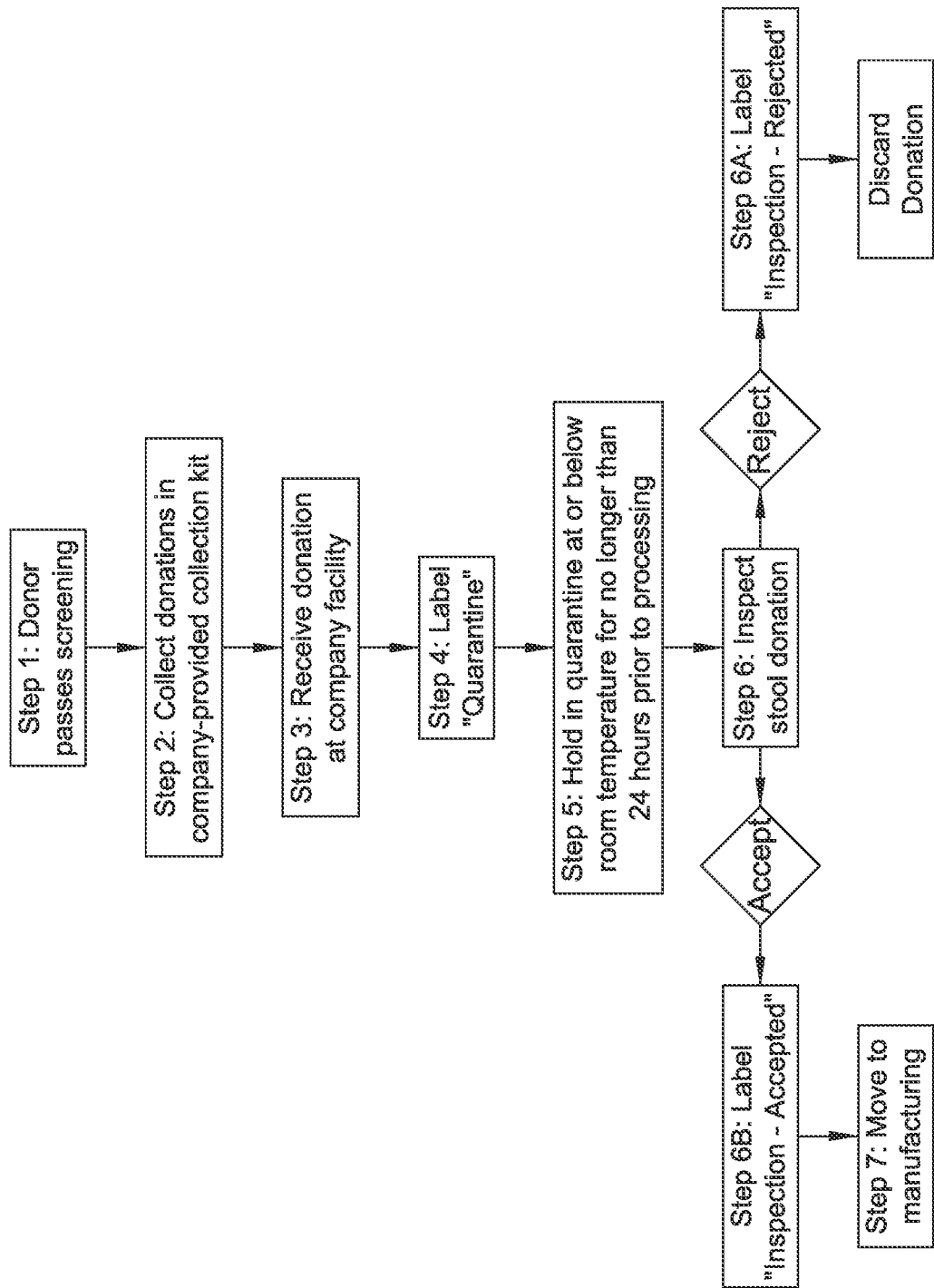
FIG. 1 is a flowchart depicting an overall process for manufacturing a standardized FMT composition; and, FIG. 2 is a flowchart depicting further steps in a representative manufacturing process.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary The following detailed description should be read with reference to the drawings in which similar elements in different drawings are numbered the same. The drawings, which are not necessarily to scale, depict illustrative embodiments and are not intended to limit the scope of the disclosure.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The term "cryopreservation," as used herein, refers to the process of cooling and storing biological cells, tissues, or organs at very low temperatures to maintain their viability. As a non-limiting example, cryopreservation can be the technology of cooling and storing cells at a temperature below the freezing point (e.g., 196 K) that permits high rates of survivability of the cells upon thawing.

The term "cryoprotectant," as used herein, refers to a substance that is used to protect biological cells or tissues from the effects of freezing.

As used herein, the term "microbiota" can refer to the human microbiome, the human microbiota or the human gut microbiota. The human microbiome (or human microbiota) is the aggregate of microorganisms that reside on the surface and in deep layers of skin, in the saliva and oral mucosa, in the conjunctiva, and in the gastrointestinal, genito-urinary, or vaginal tracts of humans. The human microbiome is comprised of bacteria, fungi, and archaea. Some of these organisms perform tasks that are useful for the human host, but the function of the majority of the organisms that make up the human microbiome is unknown. Under normal circumstances, these microorganisms do not cause disease to the human host, but instead participate in maintaining health. Hence, this population of organisms is frequently referred to as "normal flora."

The population of microorganisms living in the human gastrointestinal tract is commonly referred to as "gut flora" or "gut microbiota." The microbial flora of the human gut encompasses a wide variety of microorganisms that aid in digestion, the synthesis of vitamins, and creating enzymes not produced by the human body.

The phrase "microbiota restoration therapy," as used herein, refers to a composition which may include, but is not limited to, human fecal material containing viable gut flora from a patient or donor, a diluent, and a cryoprotectant. Additional compositions include equivalent freeze-dried and reconstituted feces or a "synthetic" fecal composition. The human fecal material is screened for the presence of pathogenic microorganisms prior to its use in the microbiota restoration therapy. The human fecal material is screened for the presence of *Clostridium* species including *C. difficile*, Norovirus, Adenovirus, enteric pathogens, antigens to *Giardia* species, *Cryptosporidia* species and other pathogens, including acid-fast bacteria, enterococci, including but not limited to vancomycin-resistant enterococci (VRE), methicillin-resistant *Staphylococcus aureus* (MSRA), as well as any ova or parasitic bodies, or spore-forming parasites, including but not limited to *Isospora, Clyslospora*, and *Cryptospora*.

The process of fecal bacteriotherapy can include introducing a fecal sample of a healthy donor, or a donor having one or more desired characteristics, into a gastrointestinal tract of a patient to repopulate a healthy or desirable gut microbiota. In certain examples, prior to introduction of the fecal sample, the patient's intestinal flora can be disrupted using antibiotics, such that the healthy or desirable gut microbiota, once introduced into the patient, can easily populate the gastrointestinal tract.

The human fecal material is optionally filtered prior to its use in the microbiota restoration therapy.

The present disclosure is directed to compositions, methods of manufacture and methods of treatment utilizing microbiota restoration therapy (MRT) for the treatment of *Clostridium difficile* infections (CDI). CDI is a common nosocomial infection and is frequently associated with severe morbidity and mortality, especially in elderly patients. While CDI treatment is one example use for the MRT compositions disclosed herein, this is not intended to be limiting. Other diseases and/or conditions are contemplated. Some of the medical conditions that may be desirably impacted by treatment with MRT compositions may include cardiovascular and/or peripheral vascular disease, allergies, obesity, hypoglycemia, constipation, celiac sprue (e.g., celiac disease), gastrointestinal cancer (e.g. gastrointestinal cancer is at least one of stomach cancer, esophageal cancer, colon cancer gallbladder cancer, liver cancer, pancreatic cancer, colorectal cancer, anal cancer, and gastrointestinal stromal tumors), myoclonus dystonia, sacrolileitis, spondyloarthropatliy, spondylarthritis, proximal myotonic myopathy; an autoimmune disease nephritis syndrome, autism, travelers' diarrhea, small intestinal bacterial overgrowth, chronic pancreatitis, a pancreatic insufficiency, chronic fatigue syndrome, benign myalgic encephalomyelitis, chronic fatigue immune dysfunction syndrome, Parkinson's Disease (PD), amyotrophic lateral sclerosis (ALS), multiple sclerosis (MS), degenerative neurological diseases, Grand mal seizures or petitmal seizures, Steinert's disease, chronic infectious mononucleosis, epidemic myalgic encephalomyelitis, idiopathic thrombocytopenic purpura (ITP), an acute or chronic allergic reaction obesity, anorexia, irritable bowel syndrome (IBS or spastic colon) Crohn's disease, irritable bowel disease (IBD), colitis, ulcerative colitis or Crohn's colitis, chronic infectious mononucleosis, epidemic myalgic encephalomyelitis, acute or chronic urticarial, lupus, rheumatoid arthritis (RA) or juvenile idiopathic arthritis (JIA), pre-diabetic syndrome, fibromyalgia (FM), Type I or Type II diabetes, acute or chronic insomnia, migraines, and attention deficit/hyperactivity disorder (ADHD).

In the case of humans, the present disclosure encompasses methods of treatment of chronic disorders associated with the presence of abnormal enteric microflora. Such disorders include but are not limited to those conditions in the following categories: gastrointestinal disorders including irritable bowel syndrome or spastic colon, functional bowel disease (FBD), including constipation predominant FBD, pain predominant FBD, upper abdominal FBD, nonulcer dyspepsia (NUD), gastro-oesophageal reflux, inflammatory bowel disease including Crohn's disease, ulcerative colitis, indeterminate colitis, collagenous colitis, microscopic colitis, chronic *Clostridium difficile* infection, pseudemembranous colitis, mucous colitis, antibiotic associated colitis, idiopathic or simple constipation, diverticular disease, AIDS enteropathy, small bowel bacterial overgrowth, coeliac disease, polyposis coil, colonic polyps, chronic idiopathic pseudo obstructive syndrome; chronic gut infections with specific pathogens including bacteria, viruses, fungi and protozoa; viral gastrointestinal disorders, including viral gastroenteritis, Norwalk viral gastroenteritis, rotavirus gastroenteritis, AIDS related gastroenteritis; liver disorders such as primary biliary cirrhosis, primary sclerosing cholangitis, fatty liver or cryptogenic cirrhosis; rheumatic disorders such as rheumatoid arthritis, non-rheumatoid arthritidies, non rheumatoid factor positive arthritis, ankylosing spondylitis, Lyme disease, and Reiter's syndrome; immune mediated disorders such as glomeruionephritis, haemolytic uraemic syndrome, juvenile diabetes mellitus, mixed cryoglobulinaemia, polyarteritis, familial Mediterranean fever, amyloidosis, scleroderma, systemic lupus erythematosus, and Behcets syndrome; autoimmune disorders including systemic lupus, idiopathic thrombocytopenic purpura, Sjogren's syndrome, haemolytic uremic syndrome or scleroderma: neurological syndromes such as chronic fatigue syndrome, migraine, multiple sclerosis, amyotrophic lateral sclerosis, myasthenia gravis, Guillain-Barre syndrome, Parkinson's disease, Alzheimer's disease, Chronic Inflammatory Demyelinating Polyneuropathy, and other degenerative disorders; psychiatric disorders including chronic depression, schizophrenia, psychotic disorders, manic depressive illness; regressive disorders including, Asbergers syndrome, Rett syndrome, attention deficit hyperactivity disorder (ADHD), and attention deficit disorder (ADD); the regressive disorder, autism; sudden infant death syndrome (SIDS), anorexia nervosa; dermatological conditions such as chronic urticaria, acne, dermatitis herpetiformis and vasculitis disorders; and cardiovascular and/or vascular disorders and diseases.

Globally, the increase in the prevalence of drug resistant organisms has created many challenges for clinicians that may pose public health risks. Infections by drug resistant organisms (e.g., vancomycin-resistant *Enterococcus* (VRE)) and *Clostridium difficile* infection share similar risk factors. VRE is a nosocomial pathogen that can be a complication among transplant and immune compromised patients. VRE carriers may also be at increased risk for infection due to VRE and also be a potential source of VRE transmissions to others. VRE shedding in stool increases with antimicrobial exposures and decreases with normalization of the intestinal microbiota after antimicrobials are discontinued. Accordingly, normalization of intestinal microbiota may not only be useful for treating *Clostridium difficile* infections (including chronic infections), these treatments may also be useful for treating infections by drug resistant organisms (e.g., VRE and/or other drug resistant organisms including those disclosed herein).

In some instances, the microbiota restoration therapy compositions (and/or fecal bacteriotherapy compositions) disclosed herein may be used to treat patients with infections by drug resistant organisms and/or multi-drug resistant organisms (MDRO). The drug resistant organisms may be resistant to antimicrobial agents (e.g., antibiotics, antivirals, antifungals, antiparasitics, other drugs, combinations thereof, and the like) and may include drug resistant microorganisms such as bacteria, viruses, fungi, parasites, etc. The infections that can be treated by the microbiota restoration therapy compositions disclosed herein may be along the digestive tract or along other systems of the patient.

The microbiota restoration therapy compositions may be used to treat infections by a variety of drug resistant organisms such as vancomycin-resistant enterococci (VRE), methicillin-resistant *Staphylococcus aureus* (MRSA), extended-spectrum β-lactamase producing gram-negative bacteria, *Klebsiella pneumoniae* carbapenemase producing gram-negative bacteria, multi-drug resistant gram negative rods bacteria (e.g., such as *Enterobacter* species, *E. coli*, *Klebsiella pneumoniae*, *Acinetobacter baumannii*, and *Pseudomonas aeruginosa*), drug resistant *Enterobacter* species, multi-drug resistant tuberculosis (e.g., *Mycobacterium tuberculosis*), drug resistant staphylococci, drug resistant enterococci, drug resistant gonococci, drug resistant streptococci (e.g., including *Streptococcus pneumoniae*), drug resistant *salmonella*, drug resistant gram negative bacteria, drug resistant *Candida*, drug resistant HIV, drug resistant influenza virus, drug resistant cytomegalovirus, drug resistant herpes simplex virus, drug resistant malaria, drug resistant *Plasmodium vivax*, drug resistant *Plasmodium falciparum*, drug resistant *Toxoplasma gondii*, and the like, and/or other drug resistant organisms. These are just examples.

Treatment of infections by drug resistant organisms with the microbiota restoration therapy compositions disclosed herein may include treating patients with no prior history of infection with a drug resistant organism, treating patients with a single prior infection by a drug resistant organism, treating patients with two or more (e.g., two, three, four, five, six, or more) prior infections by a drug resistant organism, etc. In some instances, the microbiota restoration therapy compositions may be used to treat a patient with three prior infections by a drug resistant organism. In other instances, the microbiota restoration therapy compositions may be used to treat a patient with two prior infections by a drug resistant organism if the prior infections resulted in hospitalization, if the prior or current infections require treatment with toxic drugs, or if the prior infections were all from the same organism.

In some instances, MRT compositions can be administered to a patient using an enema or other suitable technique. However, it may be desirable to orally administer an MRT composition. In order to prepare an MRT composition in a form suitable for oral administration, a number of steps may be carried out. Generally, these steps may include collecting a fecal sample, processing the fecal sample, lyophilizing or "freeze-drying" the processed fecal sample (or otherwise converting the processed fecal sample from a liquid to a solid), adding one or more additives and/or excipients, and forming an oral form of the MRT composition from the lyophilized material and additives (e.g., a tablet, capsule, liquid preparation, or the like). Some additional details regarding at least some of these steps are disclosed herein.

FIG. 1 is a flow chart depicting a portion of an example MRT production process. This is just an example. Other examples of screening donors, obtaining human stool samples, and processing the stool samples to a MRT product are disclosed in commonly assigned U.S. Patent Publication 2014/0363398, which is herein incorporated by reference. More particularly, FIG. 1 schematically depicts a process for collecting and inspecting a donor fecal sample. As a first step in the collecting/inspecting process, potential stool donors are screened. Screening/prescreening is described in more detail herein. Once the donor passes the screening, step two may include collecting the donor's stool using a human stool collection kit as defined herein, whether at home or at a collection facility. The kit can include, but is not limited to, a clean human stool collection container with lid, a large closeable/sealable bag, a donation form and a human stool collection instruction sheet. The time and date of collection, along with donor identity and method of transport, can be recorded in order to track the time from collection to processing, and the conditions of transport. As a non-limiting example, the collection container can include an indicator of the minimum and the maximum temperature to which the sample is exposed. As another non-limiting example, one or more temperature sensitive stickers that changes color at temperatures below about 4° C. and temperatures greater than about room temperature (about 22-29° C.) can be affixed to the container.

Step three may involve transporting the sample to a processing facility. It can be appreciated that if the sample is collected at the processing facility, transporting the sample is not necessary. In some instances it may be desirable to collect the sample at the processing facility in order to more clearly establish the chain of custody of the sample. With the receipt of the first stool donation for any individual, a profile will be established for each donor. Subsequent stool samples can be subjected to a human stool test, which is utilized to match and confirm the identity of the donor with the donation. Based on prior collected samples, a human stool profile for the donor is generated and can be maintained or enhanced over repeated donations. Any new sample will be compared with this profile to confirm it is the same donor. Differentiation can be made to confirm donor identity based on the representation of *Bacterioides* species in the human stool. In a non-limiting example, the base set of stool samples used to create the profile is collected at the processing facility to assure donor identity in the profile samples. In another non-limiting example, the base set of stool samples used to create the profile can be collected in locations other than the processing facility, with donor identity assurance protocols appropriate to the situation or location.

Step four of the method may include labeling the donation "Quarantine" and holding the donation in quarantine at or below room temperature for no longer than in the range of 24 hours to five days prior to processing. Donations may be rejected in situations where the temperature indicator has been activated or where the time between donation and receipt exceeds 24 hours. In addition, where applicable, the human stool test results must match the donor profile. If the human stool test does not match the donor profile, the donation collected for that day will be discarded and the donor will be disqualified.

In one method of the disclosure, the human stool sample is processed within about 24 hours of collection. In another method of the application, the time of collection is recorded at the time of arrival of the stool sample at the processing facility. Step six may include inspecting the stool donation. Visual inspection can be completed upon arrival of the stool sample at the processing facility. In the event the human stool sample is loose, unformed, is not of sufficient weight (e.g., less than about 50 g), or for any other reason, including but not limited to evidence indicating poor sample quality or concerns about donor health, the sample may be rejected, labeled "Inspection—Rejected" and the donation is discarded. Further, answers to questions on the human stool collection form can be reviewed by trained personnel. Certain answers in the collection form may require ample rejection. If the sample is accepted, it may be labeled "Inspection—Accepted" and may be moved to a manufacturing process.

Figure 2:
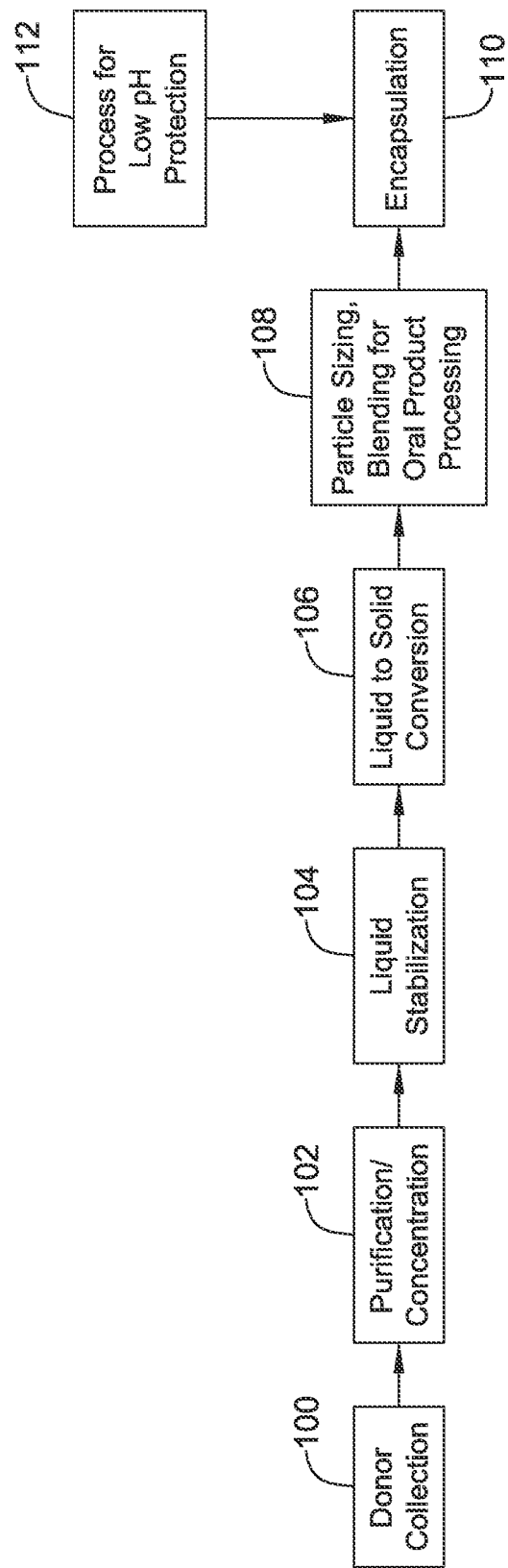

FIG. 2 is a flow chart depicting a portion of a generic illustrative method for preparing a stool sample for MRT as an oral dosage. It is contemplated that an intermediate product within the method for preparing a stool sample for MRT as an oral dosage may be suitable for MRT via an enema or gastro-nasal tube. The stool sample may first be collected and screened 100, for example, in the method described with respect to FIG. 1. Once the sample has been accepted, the sample may be purified and concentrated 102. The sample may be purified using centrifugation, membrane filtration, or a combination thereof to remove fecal material above a certain particle size. It is contemplated that since most bacteria of interest are in the range of 0.3 microns (µm) to 30 µm, the sample may be processed to remove particles greater than 50-70 µm. The sample may be processed to obtain a 75% to 90% concentration of the bacteria. This may allow for an increased flexibility in the ratio of formulation excipients to bacteria for further processing.

The sample may be membrane filtered in a number of different ways, including, but not limited to the use of filter bags, pressure filters, and/or vacuum filters. In some instances, the sample may be filtered multiple times using a smaller filter membrane with each subsequent filtering. In some instances, saline may be added as a diluent in a ratio of 1:3 (stool to saline), although this is not required. In other instances, a mixture of saline and a cryoprotectant (e.g., polyethylene glycol (PEG) 3350) may be used as a diluent. The PEG concentration of the diluent can be approximately about 30-90 g/liter (or about 10-90 g/liter). The PEG concentration of the diluent can also be approximately between about 25-75 g/liter. In one example, the ratio of saline/PEG mixture to stool sample is 2:1, or 2 mL saline/PEG mixture to 1 gram human stool. As a non-limiting example, approximately 100 mL of saline/PEG mixture can be used for 50 g of human stool. While saline/PEG may be suitable for use as a diluent (and/or cryoprotectant), this is not intended to be limiting. Other cryoprotectants may also be utilized. For example, dextrose, betaine, glycine, sucrose, polyvinyl alcohol, Pluronic F-127, mannitol, tween 80, ethylene glycol, 1,3-propanediol, hydroxypropyl cellulose, glycerol, PEG/glycerol mix, propylene glycol, or combinations thereof may be used as cryoprotectants. These materials may be used alone or in combination with a solvent such as saline.

In one example, the sample may be placed in a 500 µm filter bag, with or without a diluent, and agitated using, for example, Stomacher agitation at 230 rpm for approximately 2 minutes to obtain a filtrate having a particle size of approximately 500 µm or less. This filtrate may then be placed in a filter bag having a pore size smaller than 500 µm, for example, 280 µm. The sample may be agitated again using, for example, Stomacher agitation at 230 rpm with or without a diluent for approximately 4 minutes to obtain a filtrate having a particle size of approximately 280 µm or less. This filtrate may be placed in another filter bag having a pore size smaller than, for example, 280 µm, such as, but not limited to 60 µm. The sample may be agitated again using, for example, Stomacher agitation at 230 rpm with or without a diluent for approximately 4 minutes to produce a filtrate having a particle size of approximately 50-70 µm or less.

In another example, the sample may be placed in a 500 µm filter bag, with or without a diluent, and agitated using, for example, Stomacher agitation obtain a filtrate having a particle size of approximately 500 µm or less. This filtrate may then be processed using a pressure filter having a pore size of approximately 160 µm and the resulting filtrate processed using a pressure filter having a pore size of approximately 60 µm. In some instances, the sample may be need to be processed a second time using a bag filter having a pores size between 160 µm and 500 µm prior to using the pressure filter.

In another example, the sample may be placed in a 500 µm filter bag, with or without a diluent, and agitated using, for example, Stomacher agitation obtain a filtrate having a particle size of approximately 500 µm or less. This filtrate may then be processed using a vacuum filter having a pore size of approximately 160 µm and the resulting filtrate processed using a vacuum filter having a pore size of approximately 60 µm. In some instances, the sample may be need to be processed a second time using a bag filter having a pores size between 160 µm and 500 µm prior to using the pressure filter.

Once the sample has been processed to have a particle size of approximately 60 µm or less, the sample may then be washed and further concentrated using a centrifuge. In some instances, centrifuge tubes may have a volume in the range of 50 to 500 mL, or more. The filtered suspension is filled to approximately 20 to 80% of the volume of the centrifuge tube. In one example, the samples may be centrifuged at 1100 to 3600 revolutions per minute (rpm) for 10 to 15 minutes cycles. In another example, the samples may be centrifuged at a rate such that the centrifugal force is in the range of about 8-12,000 g (e.g., about 10,000 g) for 15-45 minutes or 20-30 minutes. The centrifuge may be ramped up or gradually accelerated to the speed needed to create a centrifugal force in the range of about 8-12,000 g (e.g., about 10,000 g). It is further contemplated that the centrifuge may also be slowly ramped down or decelerated when the centrifugation process is complete. In some instances, it may be desirable to decelerate the centrifuge as slowly as possible so that the return to atmospheric pressure is slow so as to protect the bacterial cells from potentially bursting. The supernatant is removed and the remaining material in the tube is the purified intermediate MRT composition. This may result in a product that has been concentrated by approximately 60%. In some instances, the centrifugation process may be a 2-tiered process. For example, the product may first undergo a "pre-spin" (for example 300 g for 2-5 minutes) to remove fecal fibrous material and then may undergo a longer centrifugation to concentrate the product. It is further contemplated that volumes of up to 300 mL may be centrifuged without resulting in a drop in the amount of concentration. The resulting MRT composition is a bacterial suspension having a particle size of 70 μm or less and a bacterial concentration on the order of approximately $1\times10^{10}$ CFU/g. The resulting MRT composition may also be stable for 3 weeks at refrigeration conditions.

In some embodiments, centrifugation alone can be used multiple times for purification and concentration. However, the particle size of the bacterial suspension may still be in a range (e.g. greater than 60 μm) that clogs pipet tips. However, in some instances, wide pipette tips may be used. Whether this is successful or not is dependent on the input fecal material, which is variable. It is further contemplated that a system of separators and decanters could be used if the batch size was in the range of several tens of liters, or more. However, this may not be required if the starting product has been previously processed.

In other embodiments, density gradient centrifugation may be used for purification and concentration of a fecal sample. Density gradient centrifugation may be used in combination with the filtering techniques described above, or alone. Density gradient centrifugation may separate strictly by density, whereas differential centrifugation may separate by particle size and density. To perform density gradient centrifugation, a density gradient media may be added to the sample (e.g. diluted raw sample or diluted, filtered sample). The density gradient media may be a solution of varying concentration (e.g. a sucrose having varying concentrations). For example, a density gradient media may be created by overlaying lower concentrations of a solution on higher concentrations of the solution in a centrifuge tube. The sample may be placed on top of the density gradient media and subsequently centrifuged. The particles in the sample may travel through the density gradient media until they reach the point in the gradient at which their density matches that of the surrounding solution. For example, the target material (e.g. bacteria) may settle in the middle of the centrifuge tube due to the density of the bacteria and the density gradient media. A wide variety of density gradient media may be used for the centrifugation, including, but not limited to, polyhydric (sugar) alcohols, polysaccharides, inorganic salts, iodinated compounds, colloidal silica, etc. Other density gradient materials may include iohexols such as Nycodenz® (manufactured by Axis-Shield), iodixanol solutions, such as OptiPrep™ (manufactured by Axis Shield), and/or various molecular weight PEGs. It is contemplated that concentrations in the range of 40% to 80% weight/volume (w/v) of Nycodenz® may be used. The media may be pharmaceutical grade, biologically inert, and/or isosmotic. In some instances, density gradient centrifugation may purify bacteria from stool more efficiently that differential centrifugation.

In some embodiments, tangential flow filtration (or cross-flow filtration) may be used in combination with density gradient centrifugation to further remove any undesired soluble material. In tangential flow filtration, the majority of the feed flow may flow tangentially across a surface of a filter than into the filter. Tangential flow filtration of the target material (e.g. bacteria) may further remove soluble impurities from the target material. During the tangential flow filtration, additional fibrous material may be pushed out as the bacterial suspension (obtained from traditional centrifugation and/or density gradient centrifugation) is passed across the surface of the filter. In some instances, each pass of the bacterial suspension through the tangential flow filtration system may be followed by a buffer. It is contemplated that larger volumes (e.g. up to about 10 L) of bacterial suspension may be processed at one time through a tangential flow filtration system. In some instances, the filtrate from the tangential flow filtration process may be used as the purified intermediate fecal sample. It is contemplated that the filtered suspension (e.g. filtrate) may be diluted with saline and/or phosphate-buffered saline (PBS). In other instances, the filtrate from the tangential flow filtration process may be further processed using, for example, but not limited to, differential centrifugation and/or dead-end filtration.

In some embodiments, it may be desirable to stabilize the processed sample in suspension 104 at refrigeration conditions for a period of time in the range of one to two weeks. In some instances, removal of the fecal material and replacement with carriers or excipients which are soluble in an aqueous solution may allow the bacteria to be suspended in the liquid and further processed without stability concerns. Considerations for these excipient solutions may be pH, concentration, and isotonicity or isosmolality. Excipients may be selected based on protein and monoclonal antibody formulations and their proposed role in stabilizing biologics. Some example excipients that may be used to provide liquid stabilization 104 of the sample may include, but are not limited to: salt (NaCl), sucrose, trehalose, L-arginine monohydrochloride, and/or PEG 3350, as summarized in Table 1 below. Lists of other potential excipients can be found in tables I and III in Seong Hoon Jeong, Arch Pharm Res Vol 35, No 11, 1871-1886, 2012 and in Tables in Pramanick et al. Pharma Times, Vol 45, No. 3, March 2013.

TABLE 1

Summary of illustrative excipients.

| Excipient | MW (g/mol) | Solution % | M (g/mol) |
|---|---|---|---|
| NaCl | 58.44 | 0.9 | 0.15 |
| Sucrose | 342.3 | 6 | 0.18 |
| Sucrose | 342.3 | 9.25 | 0.27 |
| Sucrose | 342.3 | 12 | 0.35 |
| L-Arginine Monohydrochloride | 210.66 | 0.5 | 0.02 |
| L-Arginine Monohydrochloride | 210.66 | 1.5 | 0.07 |
| L-Arginine Monohydrochloride | 210.66 | 3 | 0.14 |
| PEG 3350 | 3350 | 1 | 0.00 |
| PEG 3350 | 3350 | 5 | 0.01 |
| PEG 3350 | 3350 | 10 | 0.03 |
| L-Arginine Monohydrochloride | 210.66 | 0.17 | 0.01 |

In some instances, the excipient may include 2-20% sucrose, 0.1-5% L-arginine monohydrochloride, 0.5-20% PEG 3550, or combinations thereof.

Combinations of excipients may be used to protect biological cells or tissues from the effects of freezing and/or to provide stability (e.g. minimize cell death) to the product during storage. Table 2 below illustrates some example excipient formulations that may provide cryoprotection and stability during storage. However, the formulations listed in Table 2 are not intended to be limiting. Other combinations and/or quantities of excipients may also be used.

TABLE 2

| | Component 1 | Component 2 | Component 3 | Component 4 | Component 5 |
|---|---|---|---|---|---|
| | Excipient Solution Compositions Prior to Adding to the Drug Substance | | | | |
| #1 | 20%, PEG-120 Methyl Glucose Dioleate | 60%, Sucrose | 20%, Phosphate Buffer Solution, pH 7.4 | | |
| #2 | 20%, PEG-120 Methyl Glucose Dioleate | 60%, Trehalose | 20%, Phosphate Buffer Solution, pH 7.4 | | |
| #3 | 20%, Polyvinylpyrrolidone (PVP) | 60%, Sucrose | 20%, Phosphate Buffer Solution, pH 7.4 | | |
| #4 | 20%, Polyvinylpyrrolidone (PVP) | 60%, Trehalose | 20%, Phosphate Buffer Solution, pH 7.4 | | |
| #5 | 20%, PEG-120 Methyl Glucose Dioleate | 20%, Polyvinylpyrrolidone (PVP) | 40%, Sucrose | 20%, Phosphate Buffer Solution, pH 7.4 | |
| #6 | 20%, PEG-120 Methyl Glucose Dioleate | 20%, Polyvinylpyrrolidone (PVP) | 40%, Trehalose | 20%, Phosphate Buffer Solution, pH 7.4 | |
| #7 | 2.3% Polyethylene Glycol 3350 | 10% Trehalose | 10% Sucrose | 1% Glycerin | 76.7% Purified Water |

It is contemplated that the above excipient formulations, when added to the drug substance (e.g. fecal sample or processed fecal sample) may provide cryoprotection and stability during storage to the biological cells in a liquid and/or solid formulation. In some instances, the excipient formulations may be added to the drug substance in a ratio of 1:1. This is just an example. Other excipient to drug substance ratios are also contemplated, for example, but not limited to 0.25:1, 0.5:1, 1.5:1, 2:1, etc.

In some of these and in other instances, the excipient formulations may include: (a) 0.5-20% PEG, (b) 0.1-5% glycerin, (c) 10-30% PVP, (d) 40-80% trehalose, (e) 40-80% sucrose, (f) 10-30% phosphate buffer solution, or (g) combinations thereof. Other formulations are contemplated.

It is contemplated that similar excipients may also be used to protect the bacteria during membrane filtration. For example, Farber and Sharpe in Applied and Environmental Microbiology, August 1984, P. 441-443 state that bacterial recovery is improved in the presence of certain food debris (carrots, cheese, peaches, tuna)—pH may be important—pH 5.88 to 6.40 for carrots, pH 4.75-5.02 for cheese, pH 5.9 to 6.2 for tuna, pH 3.3 to 4.05 for peaches. The presence of sugars, carbohydrates, or proteins may be important, properties of these foods that coat the bacteria, support bacterial growth (pre-biotic activity) or support the bacterial cell wall during filtration may be important.

Suitable carriers may vary with the desired form and mode of administration of the composition. For example, they may include diluents or excipients such as fillers, binders, wetting agents, disintegrators, surface-active agents, glidants, lubricants, and the like. Typically, the carrier may be a solid (including powder), liquid, or combinations thereof. Each carrier is preferably "acceptable" in the sense of being compatible with the other ingredients in the composition and not injurious to the subject. The carrier may be biologically acceptable and inert (e.g., it permits the composition to maintain viability of the biological material until delivered to the appropriate site).

Oral compositions may include an inert diluent or an edible carrier. For the purpose of oral therapeutic administration, the active compound can be incorporated with excipients and used in the form of tablets, troches, or capsules, e.g., gelatin capsules. Oral compositions can also be prepared by combining a composition of the present disclosure with a food. In one embodiment a food used for administration is chilled, for instance, ice cream. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, orange flavoring, or other suitable flavorings. These are for purposes of example only and are not intended to be limiting.

Once the purified sample has been purified and stabilized in an aqueous suspension which may be suitable for delivery via a gastro-nasal tube or an enema, the sample may be further processed to be suitable for an oral delivery, such as in the form of tablets, troches, or capsules. For example, the aqueous solution may be converted to a solid 106. A list of bacterial processing techniques can be found in Martin et al., Innovative Food Science and Emerging Technologies, 27 (2015) 15-25.

In some instances, lyophilization, or freeze-drying, may be used to convert the sample from a liquid to a solid. The sample may be provided with a cryoprotectant such as, but not limited to PEG, skim milk, charcoal, ascorbic acid or a combination thereof to protect the bacteria from the effects of freezing. The sample may also be provided with a lyoprotectant such as, but not limited to sucrose, inositol, trehalose, glycerol, or a combination thereof. In some instances, the sample may also be provided with an enrichment material which may provide acid buffering. Alternatively or additionally, the enrichment material may also keep the bacteria more active which may facilitate analytical testing. Some example enrichment materials may include, but are not limited to skim milk, charcoal, gelatin, ascorbic acid, GI media, or combinations thereof. Alternatively or additionally, an oxygen scavenger may be added to the sample prior to and/or after lyophilization. While not wishing to be bound by theory, it is believed that an oxygen scavenger may improve the stability and/or viability of the sample. It is contemplated that lyophilization tubes may include an insert that can be used to expel a lyophilized pellet from the lyophilization tube after freeze-drying. The width of the lyophilization tube may be smaller than the width of a capsule shell for oral treatment. This may allow for the displacement of a tray of pellets directly into the capsule shells. It is contemplated that this may reduce or eliminate the need for particle sizing of the formulation or blending it further 108 for improvement in flow properties into the capsule. The dose may also be determined by pellet size. In some instances, a pellet produced in the lyophilization process may include approximately $4.5 \times 10^8$ CFU (CDC). A size 0 capsule may accommodate three pellets. Thus, a capsule may include approximately $6.7 \times 10^9$ CFU (CDC). Eight capsules taken twice a day may be required to be equivalent to one enema dose. Further, there may be no need to test for homogeneity of the batch of pellets that are mixed together prior to capsule filling. In some instances, tamping may allow for a greater concentration or number of pellets within each capsule. For example, tamping of the pellets within the capsule may allow for about 2-4 times (e.g., about 2.5 times) the number of pellets in each capsule (e.g., without tamping each capsule may accommodate 2-4 or about 3 pellets whereas with tamping each capsule may accommodate about 7-10 or about 8 pellets). This may help to reduce the number of capsules a patient may need to take in order to achieve the desired dose. In some instances, the pellets may be ground prior to tamping them into the capsule. If the pellets are ground, it may be desirable for the powder to have a Carr's Index value in the range of 15 to 30 to facilitate capsule filling. Alternatively, the pellets may be ground and compressed into a tablet form. An enteric powder may then be pressed over the tablet to generate an oral dosage that may be stable in the acid environment of the stomach but dissolves in the intestinal tract.

In other instances, it may be desirable to preserve the sample through vaporization foam drying. It is contemplated that traditional excipients and equipment may be used with this process. Higher excipient concentrations and optimal process parameters to produce foam during processing may result in low water content formulations. The lower the water content; the greater the probability of stability at room temperature. Once the sample has been dried 106, the sample may be further processed to achieve a desired particle size and/or blending 108 in order to prepare the sample for oral product processing.

In yet other embodiments the liquid sample may be microencapsulated by lipids to protect from bile, alginates, and/or polymers. Once the sample has been encapsulated, the sample may be further processed to achieve a desired particle size and/or blending 108 in order to prepare the sample for oral product processing.

After the sample has been processed to a desired particle size and/or blended 106 in order to prepare the sample for oral product processing, the sample may be encapsulated 110. It is contemplated that the encapsulation process may provide for low pH protection 112. For example, the encapsulation process may prevent or substantially prevent capsule shells, tablets, and/or troches from breaking down in the acidic environment of the stomach such that the MRT composition is released in the desired portion of the intestinal tract. It is contemplated that an enteric coated capsule may be needed to provide for protection in the stomach and have disintegration of the capsule in the small and large intestine. In some instances, the capsules may be pan coated with the enteric coating. Enteric coating materials may include fatty acids, waxes, shellac, plastics, and plant fibers. Pan coating of hydroxypropyl methylcellulose (HPMC), or also called Hypromellose capsules, will protect at low pH and also help to protect from moisture. Some suitable capsules may include DRcaps™ and Vcaps™ available from Capsugel®. Likewise, AR caps having a composition of 60% HPMC and 40% HPMCP (hypromellose phthalate) may have the same properties. Capsule types that are not gelatin may contain less water (gelatin caps usually 10 to 12% water, versus other polymer capsules have 3-4% or less water). Banding of the capsule with polymers that are insoluble in low pH environments may be required, as will be discussed in more detail below. In other instances, the capsules may be stacked such that 2 or more capsules are used to enclose the sample. For example, the sample may be placed in a capsule and then that capsule placed in another larger capsule. A stacked (e.g. two or more capsules) and/or banded capsule may survive in an acidic environment (e.g. the stomach) for at least two or more hours and dissolve in the more neutral intestinal tract.

In some instances, in the absence of a band securing the capsule components together, the capsule may undesirably open or break apart in the stomach. For example, an unbanded capsule may open within less than 30 minutes or even less than 15 minutes after being ingested. This may cause the product to be prematurely released within the stomach instead of in the intestines where it is more desirable. In contrast, a capsule that has been banded with a low pH-resistant polymer may not fully disintegrate and/or release the product for 5 or more hours. This may allow the capsule to pass through the stomach intact and allow the product to be released into the intestines where the bacteria is desired. It is further contemplated that releasing the MRT composition into the more neutral environment of the intestines, as opposed to the acidic environment of the stomach (in the range of a pH of 1.2) may allow more bacteria to survive. Banding the capsule may include placing a band of low pH-resistant polymer over the region where the first capsule portion and the second capsule portion overlap.

In some embodiments, superdisintegrants may be used to expand the dosage form (e.g. capsule or tablet) to improve the probability of bacteria contacting the intestinal wall. For example, cross-linked cellulose swells 4 to 8 times in 10 seconds, cross-linked starch swells 7 to 12 times in less than 30 seconds, and cross-linked alginic acid experiences rapid swelling in an aqueous medium or wicking action.

The presence of pre-biotics may be desired to ensure bacterial growth at site of action in the intestine. These are materials that can be added to the capsule formulation or dosed separately at the same administration time. Some suitable additives may include galacto-oligosaccharides, inulin-derivatives such as fructo-oligosaccharides, cellulose, dextrins, chitins, pectins, beta-glucans, waxes, lignin, phytochemicals (bioactive non-nutrient plant compounds present in fruits, vegetables, grains, and other plant foods), carotenoids, phenolics, alkaloids, nitrogen-containing and organosulfur compounds. It is contemplated that L-arginine and PEG excipients, in certain concentration ranges, may produce water and electrolyte secretion when the drug product is delivered. This may enhance the bacteria's ability to attach and grow in the intestine. Other excipients that produce this effect may also improve the therapeutic effect.

An oral product may be packaged in a number of different ways including, but not limited to, blister packaging or a bottle. In some instances, an oxygen scavenger and/or a desiccant may be placed in the bottle and/or blister packaging. The blister packaging and/or bottle may include features configured to make the packing child resistant. For example, a bottle may be provided with a child resistant cap and the blister pack may be provided with a child resistant outer sleeve. In some instances, the blister pack may include graphics designed to guide the patient on how to use the pack. For example, the blister pack may provide guidance on how many pills to take on a given day and/or what time of day to take the pills. The packaging may include monitoring devices to monitor the shipping conditions. As a non-limiting example, the packaging containers can include an indicator of the minimum and the maximum temperature to which the product is exposed. As another non-limiting example, one or more temperature sensitive stickers that changes color at temperatures below about 4° C. and temperatures greater than about room temperature (about 22-29° C.) can be affixed to the container.

Figure 3:
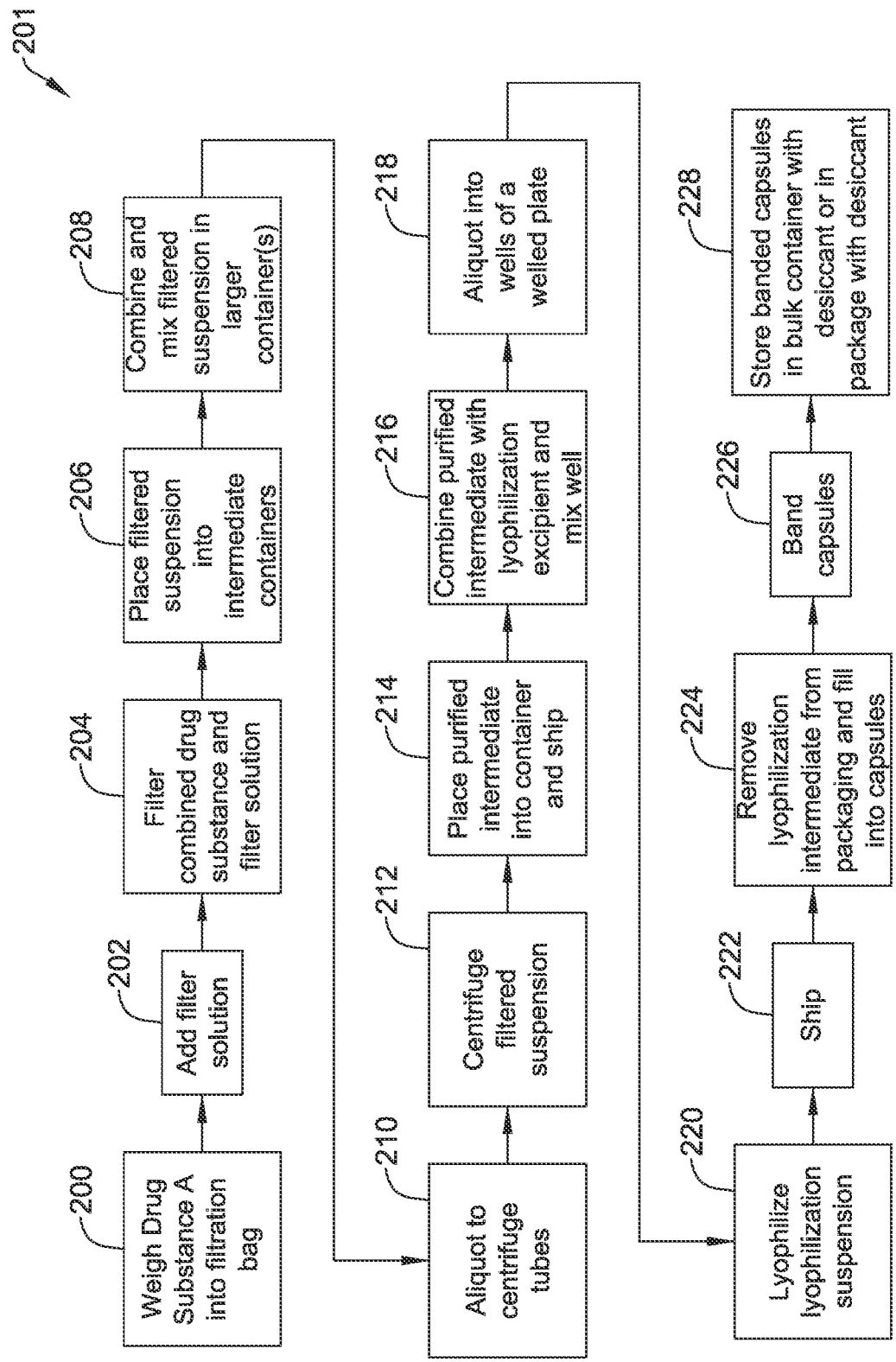
FIG. 3 is a flowchart depicting further steps in another representative manufacturing process.
Figure 4:
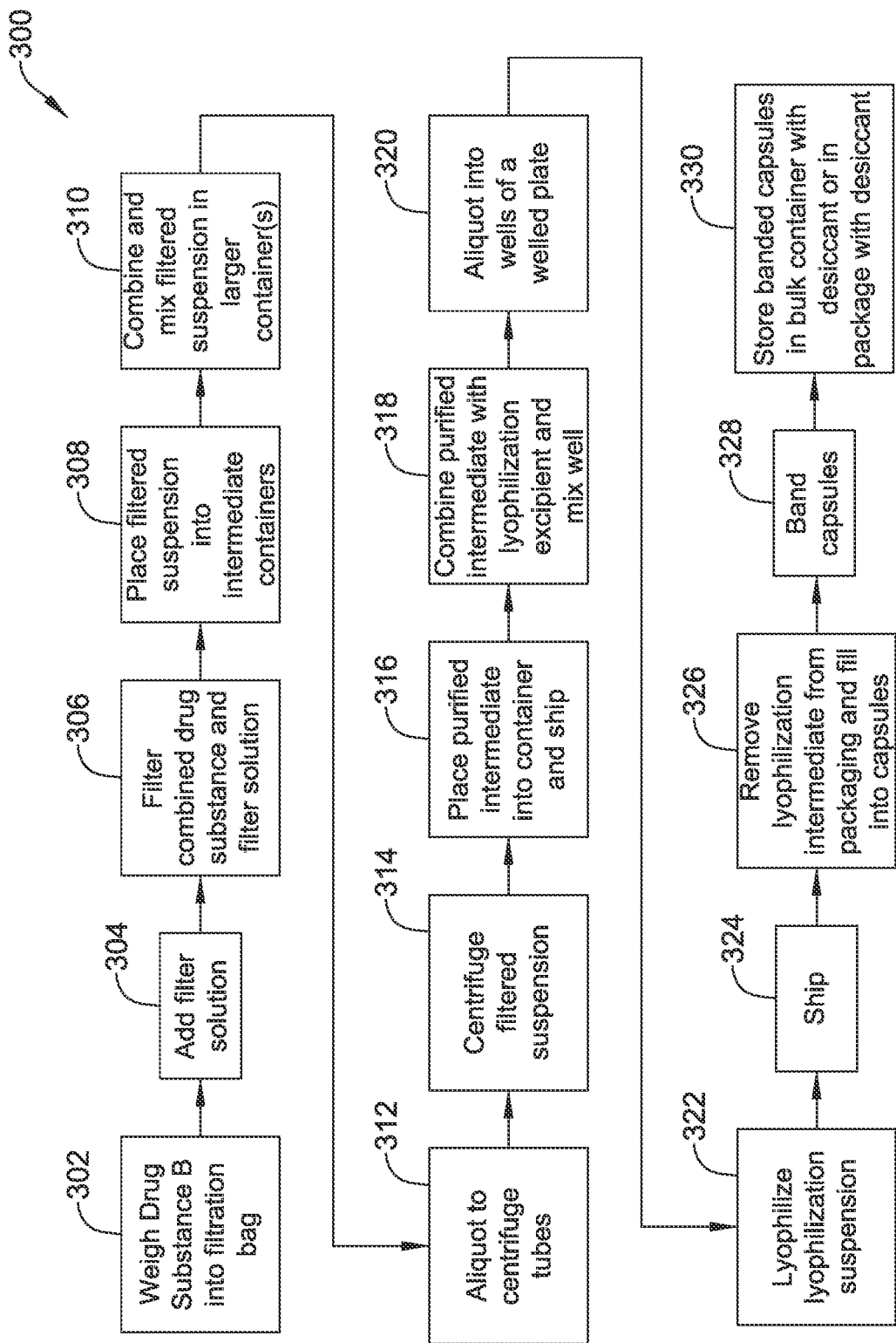
FIG. 4 is a flowchart depicting further steps in another representative manufacturing process.

FIGS. 3 and 4 are a flow charts depicting two illustrative methods 201, 300 for preparing a stool sample for MRT as an oral dosage. In some embodiments, the oral dosage may be prepared from a fresh stool sample (FIG. 3) and in other embodiments, the oral dosage may be prepared from a substance that has already been processed (FIG. 4). As used herein a fresh stool sample will be referred to as Drug Substance A and a sample that has been previously processed will be referred to as Drug Substance B. Other drug substances are contemplated includes substances derived from cultures of fecal microbiota. Referring first to FIG. 3, the stool sample may first be collected and screened, for example, in the method described with respect to FIG. 1. Once the sample has been accepted, the sample may be weighed into a filtration bag, as shown at step 200. It is contemplated that multiple collection containers (e.g. same or different donors and collected at various times) that are within their expiration data may be used (e.g. pooled together). The sample may be purified using centrifugation, membrane filtration, or a combination thereof to remove fecal material above a certain particle size. It is contemplated that since most bacteria of interest are in the range of 0.3 microns ($\mu$m) to 30 $\mu$m, the sample may be processed to remove particles greater than in the range of 50-70 $\mu$m. The sample may be processed to obtain an approximately 60% concentration of the bacteria. This may allow for an increased flexibility in the ratio of formulation excipients to bacteria for further processing.

A filter solution, or diluent, may be added to the filter bag, as shown at step 202. In some instances saline may be used as a diluent. For example a solution of 0.9% sodium chloride (NaCl) may be added to the filter bag at a ratio of approximately 3 milliliters (mL) per gram of Drug Substance A. It is contemplated that other diluents, other diluent concentrations, and dilution rates may be used, as desired. For example, a mixture of saline and a cryoprotectant (e.g., polyethylene glycol (PEG) 3350) may be used as a diluent. The PEG concentration of the diluent can be approximately about 30-90 g/liter (or about 10-90 g/liter). The PEG concentration of the diluent can also be approximately between about 25-75 g/liter. In one example, the ratio of saline/PEG mixture to stool sample is 2:1, or 2 mL saline/PEG mixture to 1 gram human stool. However, in some instances, such as when Drug Substance A is being processed specifically for lyophilization, the diluent may not include a cryoprotectant. The sample may then be membrane filtered in a number of different ways, including, but not limited to the use of filter bags, pressure filters, and/or vacuum filters, as shown at step 204. In some instances, the sample may be filtered multiple times using a smaller filter membrane with each subsequent filtering. In one example, the sample may be placed in a 500 $\mu$m filter bag and agitated using, for example, Stomacher agitation at 230 rpm for approximately 2 minutes to obtain a filtrate having a particle size of approximately 500 $\mu$m or less. This filtrate may then be placed in a filter bag having a pore size smaller than 500 $\mu$m, for example, 280 $\mu$m. The sample may be agitated again using, for example, Stomacher agitation at 230 rpm with or without a diluent for approximately 4 minutes to obtain a filtrate having a particle size of approximately 280 $\mu$m or less. This filtrate may be placed in another filter bag having a pore size smaller than, for example, 280 $\mu$m, such as, but not limited to 50-70 $\mu$m. The sample may be agitated again using, for example, Stomacher agitation at 230 rpm with or without a diluent for approximately 4 minutes to produce a filtrate having a particle size of approximately 50-70 $\mu$m or less.

In another example, the sample may be placed in a 500 $\mu$m filter bag, with or without a diluent, and agitated using, for example, Stomacher agitation obtain a filtrate having a particle size of approximately 500 $\mu$m or less. This filtrate may then be processed using a pressure filter having a pore size of approximately 160 $\mu$m and the resulting filtrate processed using a pressure filter having a pore size of approximately 60 $\mu$m. In some instances, the sample may be need to be processed a second time using a bag filter having a pores size between 160 $\mu$m and 500 $\mu$m prior to using the pressure filter.

In another example, the sample may be placed in a 500 $\mu$m filter bag, with or without a diluent, and agitated using, for example, Stomacher agitation obtain a filtrate having a particle size of approximately 500 $\mu$m or less. This filtrate may then be processed using a vacuum filter having a pore size of approximately 160 $\mu$m and the resulting filtrate processed using a vacuum filter having a pore size of approximately 60 $\mu$m. In some instances, the sample may be need to be processed a second time using a bag filter having a pores size between 160 $\mu$m and 500 $\mu$m prior to using the pressure filter.

Once the sample has been processed to have a particle size of approximately 50-70 $\mu$m or less, the sample may then be placed into intermediate storage containers, as shown at step 206. An example of an acceptable intermediate storage container is a 250 mL sterile plastic container with lid. In some instances, the filtered suspension may be stored in the refrigerator at 5±3° C. for up to 5 days, although this is not required. The filtered suspension may be combined and mixed into larger containers, as shown at step 208. An example of an acceptable immediate storage container is a multiple liter sterile plastic container with lid.

Aliquots of the mixed filtered suspension may then be placed into centrifuge tubes, 50 to 500 mL in volume, as shown at step 210. The filtered suspension is filled to approximately 20 to 80% of the volume of the centrifuge tube. In some instances, centrifuge tubes having a volume of greater than 500 mL may be used. The filtered suspension may then be washed and further concentrated using a centrifuge, as shown at step 212. In one example, the samples may be centrifuged at 1100 to 3600 revolutions per minute (rpm) for 10 to 15 minutes cycles. In another example, the samples may be centrifuged at a rate such that the centrifugal force is in the range of about 8-12,000 g (e.g., about 10,000 g) for 15-45 minutes or 20-30 minutes. The centrifuge may be ramped up or gradually accelerated to the speed needed to create a centrifugal force in the range of about 8-12,000 g (e.g., about 10,000 g). It is further contemplated that the centrifuge may also be slowly ramped down or decelerated when the centrifugation process is complete. In some instances, it may be desirable to decelerate the centrifuge as slowly as possible so that the return to atmospheric pressure is slow so as to protect the bacterial cells from potentially bursting. The supernatant is removed and the remaining material in the tube is the purified intermediate MRT composition. This may result in a product that has been concentrated by approximately 60%.

In some instances, the centrifugation process may be a 2-tiered process. For example, the product may first undergo a "pre-spin", (for example 300 g for 2-5 minutes) to remove fecal fibrous material and then may undergo a longer centrifugation to concentrate the product. It is further contemplated that volumes of up to 300 mL may be centrifuged without resulting in a drop in the amount of concentration. In some instances, volumes of greater than 300 mL may be centrifuged. For example, as discussed above, the centrifuge volume may be selected as a percentage (for example, in the range of 60%) of the container volume. The resulting MRT composition is a bacterial suspension having a particle size of 70 µm or less and a bacterial concentration on the order of approximately $1 \times 10^{10}$ CFU/g. The purified intermediate bacterial viability may be measured via a propidium monoazide (PMA) quantitative polymerase chain reaction (qPCR) method. The resulting MRT composition may also be stable for 3 weeks at refrigeration conditions.

In some embodiments, centrifugation alone can be used multiple times for purification and concentration. However, the particle size of the bacterial suspension may still be in a range (e.g. greater than 60 µm) that clogs pipet tips. Whether this is successful or not is dependent on the input fecal material, which is variable. It is further contemplated that a system of separators and decanters could be used if the batch size was in the range of several tens of liters, or more.

The intermediate MRT composition may be optionally transferred to an intermediate tube and, if necessary, shipped to a lyophilization facility, as shown at step 214. Purified intermediate may be shipped in a pre-qualified shipper for refrigeration conditions, 5±3° C. to the contract lyophilizer, if necessary, for lyophilization.

The purified intermediate may be mixed at a 1:1 ratio with a lyophilization excipient solution, as shown at step 216. The lyophilization excipient solution may be comprised of 2.3% PEG 3350, 1% glycerin, 10% trehalose, and 10% sucrose. However, other lyophilization excipients may be used. Prior to adding the excipient solution to the purified intermediate, the lyophilization excipient solution (without glycerin) is filtered through a 0.2 µm filter. The glycerin is autoclaved at 121° C. for a minimum of 15 minutes and added aseptically. Once the lyophilization excipients and purified intermediate have been mixed (lyophilization suspension), a single two hundred microliter (200 µL) aliquot of the lyophilization suspension is placed in each well of a 96-well plate, as shown at step 218 and lyophilized, as shown at step 220.

Figure 5:
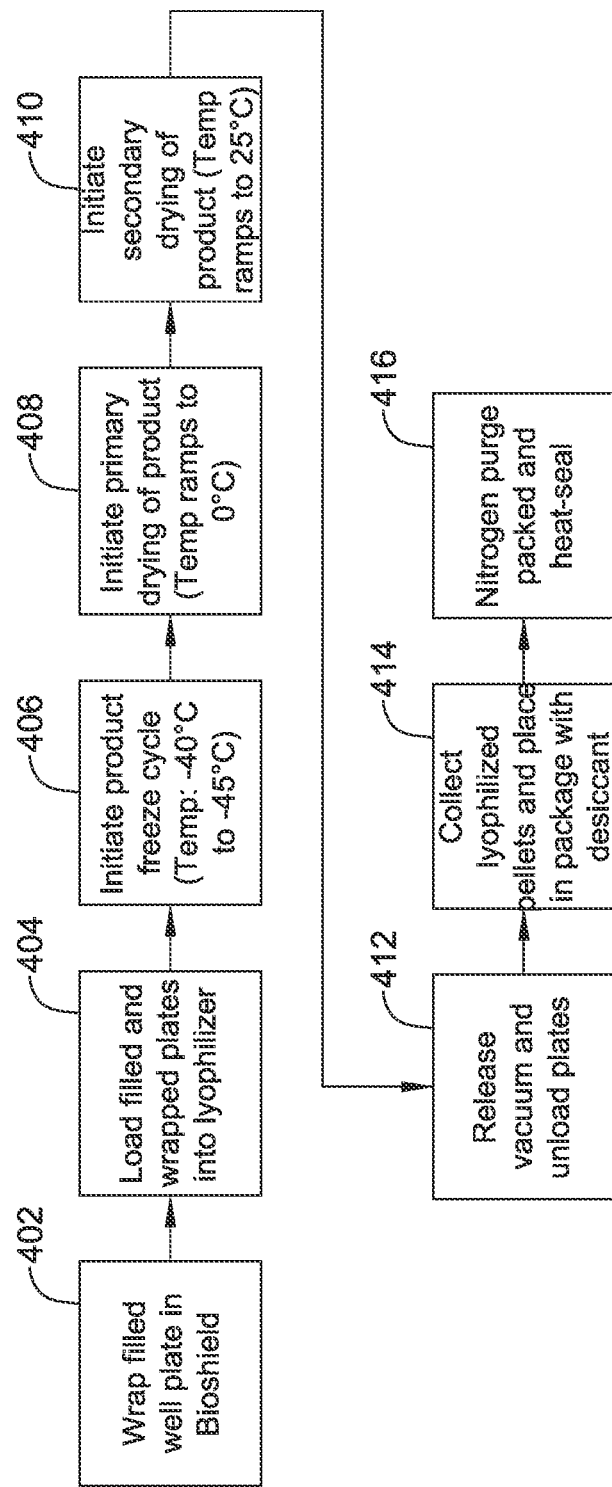
FIG. 5 is a flowchart depicting further steps in another representative manufacturing process.

The lyophilization process will be described with further reference to FIG. 5, which illustrates a flow chart of an illustrative lyophilization process 220. To perform the lyophilization, once filled, the 96-well plate may be wrapped in sterile bioshield, as shown at step 402. Other plate sizes are also contemplated. After all plates are wrapped, they may be immediately transported and loaded into the lyophilizer, as shown at step 404. The lyophilizer may be sealed and the lyophilization cycle initiated. Product is frozen by lowering the product shelf temperature to a range of approximately −40° C. to −45° C., as shown at step 406. After the product is frozen, primary drying (sublimation) occurs by applying vacuum and elevating the shelf temperature up to 0° C., as shown at step 408. A secondary drying step is initiated to further reduce water content and bring the product to ambient temperature (approximately 25° C.), as shown at step 410. The vacuum is released at the end of the secondary drying step and the product is removed from the lyophilizer, as shown at step 412. Product may be placed inside an anaerobic chamber for collection of the lyophilized aliquots. The lyophilized aliquots may be in pellet form and are transferred to a packaging with desiccant, as shown at step 414. Filled packages may be purged with nitrogen gas and heat-sealed, as shown at step 416. Returning now to FIG. 3, if the intermediate MRT composition has been shipped off-site for lyophilization, the lyophilized pellets may then be shipped back to the MRT composition manufacturer, in a pre-qualified shipper for refrigeration conditions, as shown at step 222.

In some instances, it may be desirable for the lyophilized material or pellets to have a glass transition temperature ($T_g$) of greater than 30° C. In some examples, the glass transition temperature may be in the range of 30-75° C. This may result in a final product that is stable at room temperature. The glass transition temperature may also be used as a tool for screening the product received form the lyophilization process and/or for verifying the stablility of the final product. For example, the $T_g$ may be used to predict stability of the product during storage. In some instances, a $T_g$ of 50° C. above the storage temperature may allow the lyophilized intermediate and/or the final oral drug product to be stored for a period of time without a significant loss of bacteria.

Upon receipt of the lyophilized intermediate, it may be removed from the packaging and filled into capsules, as shown at step 224. The lyophilized intermediate may also be sampled and the total viability is measured via a PMA-qPCR method. Encapsulation may be conducted in a nitrogen-purged area at ambient temperature to minimize the exposure of the lyophilized intermediate to oxygen. The lyophilization intermediates are encapsulated in a hypromellose capsule. Multiple lyophilized intermediates can be loaded into a hypromellose capsule depending on the capsule size (e.g., sizes 1, 0, or 00).

The capsule may then be banded, as shown at step 226. In some instances, the capsules may be banded with hypromellose. In some instances, the banding material may be an anionic copolymer based on methacrylic acid and methyl methacrylate, such as, but not limited to Eudragit® L100. In other instances, the banding material may be hypromellose phthalate or hypromellose acetate succinate. These are just examples. The banding material may be any material which is resistant to low pH environments (e.g. the stomach) and degrades in high pH environments (e.g. the intestinal tract). A consistent banding thickness is applied to each capsule so the disintegration performance meets the acceptance limit. Capsules are stored at refrigeration conditions, 5±3° C. in a nitrogen-purged bulk plastic container or packaged with desiccant. Encapsulated and banded drug product may be packaged with desiccant and heat-sealed, as shown at step 228. In some instances, the encapsulated and banded drug product may be packaged in individual dosage quantities in metallized polyester/polyethylene bonded film. This may minimize the exposure of the drug product to oxygen and/or moisture which may cause degradation of the product. The metallized polyester/polyethylene bonded film may have a moisture vapor transmission rate of 0.02 gr/100 in$^2$ and an oxygen transmission rate of 0.0402/mL/100 in$^2$ in 24 hours. The bonded film packets may be provided to the patient in a child-resistant container to meet the need for child-resistant clinical supply packaging. The child-resistant container may be a 40 dram (2.5 ounces) green pharmacy vial with a child-resistant cap. The vial may be made of translucent, light resistant polypropylene. The low density polyethylene (LDPE) child-resistant cap helps prevent unauthorized access by requiring that the user push down and rotate the cap to open the container.

Referring now to FIG. 4, an illustrative method 300 for preparing a previously purified stool sample (Drug Substance B) for MRT as an oral dosage. Drug Substance B may be a fecal microbiota frozen preparation, prepared as an enema dosage form including human stool and a solution of 2.3% polyethylene glycol 3350 (or other cryoprotectant) and 0.9% sodium chloride solution for irrigation in a ratio 1 g of stool to 3 mL of solution. For example, Drug Substance B may have been processed in a manner similar to steps 200 through 212 described above, with the addition of a cryoprotectant at step 202. After the centrifugation process outlined at step 212, the purified intermediate (e.g. now Drug Substance B) may be refrigerated, frozen, or used for treatment.

Beginning at step 302, the frozen preparation may be thawed, if necessary, and placed into a filtration bag. It is contemplated that multiple collection containers (e.g. same or different donors and collected at various times) that are within their expiration data may be used. The sample may be purified using centrifugation, membrane filtration, or a combination thereof to remove fecal material above a certain particle size. It is contemplated that since most bacteria of interest are in the range of 0.3 microns ($\mu m$) to 30 $\mu m$, the sample may be processed to remove particles greater than in the range of 50-70 $\mu m$. The sample may be processed to obtain an approximately 60% concentration of the bacteria. This may allow for an increased flexibility in the ratio of formulation excipients to bacteria for further processing.

A filter solution, or diluent, may be added to the filter bag, as shown at step 304. In some instances saline may be used as a diluent. For example a solution of 0.9% sodium chloride (NaCl) may be added to the filter bag at a ratio of approximately 3 milliliters (mL) per gram of Drug Substance B. It is contemplated that other diluents, other diluent concentrations, and dilution rates may be used, as desired. The sample may then be membrane filtered in a number of different ways, including, but not limited to the use of filter bags, pressure filters, and/or vacuum filters, as shown at step 306. In some instances, the sample may be filtered multiple times using a smaller filter membrane with each subsequent filtering. In one example, the sample may be placed in a 500 $\mu m$ filter bag and agitated using, for example, Stomacher agitation at 230 rpm for approximately 2 minutes to obtain a filtrate having a particle size of approximately 500 $\mu m$ or less. This filtrate may then be placed in a filter bag having a pore size smaller than 500 $\mu m$, for example, 280 $\mu m$. The sample may be agitated again using, for example, Stomacher agitation at 230 rpm with or without a diluent for approximately 4 minutes to obtain a filtrate having a particle size of approximately 280 $\mu m$ or less. This filtrate may be placed in another filter bag having a pore size smaller than, for example, 280 $\mu m$, such as, but not limited to 50-70 $\mu m$. The sample may be agitated again using, for example, Stomacher agitation at 230 rpm with or without a diluent for approximately 4 minutes to produce a filtrate having a particle size of approximately 50-70 $\mu m$ or less.

In another example, the sample may be placed in a 500 $\mu m$ filter bag, with or without a diluent, and agitated using, for example, Stomacher agitation obtain a filtrate having a particle size of approximately 500 $\mu m$ or less. This filtrate may then be processed using a pressure filter having a pore size of approximately 160 $\mu m$ and the resulting filtrate processed using a pressure filter having a pore size of approximately 60 $\mu m$. In some instances, the sample may be need to be processed a second time using a bag filter having a pores size between 160 $\mu m$ and 500 $\mu m$ prior to using the pressure filter.

In another example, the sample may be placed in a 500 $\mu m$ filter bag, with or without a diluent, and agitated using, for example, Stomacher agitation obtain a filtrate having a particle size of approximately 500 $\mu m$ or less. This filtrate may then be processed using a vacuum filter having a pore size of approximately 160 $\mu m$ and the resulting filtrate processed using a vacuum filter having a pore size of approximately 60 $\mu m$. In some instances, the sample may be need to be processed a second time using a bag filter having a pores size between 160 $\mu m$ and 500 $\mu m$ prior to using the pressure filter.

Once the sample has been processed to have a particle size of approximately 50-70 $\mu m$ or less, the sample may then be placed into intermediate storage containers, as shown at step 308. An example of an acceptable intermediate storage container is a 250 mL sterile plastic container with lid. In some instances, the filtered suspension may be stored in the refrigerator at 5±3° C. for up to 5 days, although this is not required. The filtered suspension may be combined and mixed into larger containers, as shown at step 310. An example of an acceptable immediate storage container is a multiple liter sterile plastic container with lid.

Aliquots of the mixed filtered suspension may then be placed into centrifuge tubes, 50 to 500 mL in volume, as shown at step 312. The filtered suspension is filled to approximately 20 to 80% of the volume of the centrifuge tube. In some instances, centrifuge tubes having a volume of greater than 500 mL may be used. The filtered suspension may then be washed and further concentrated using a centrifuge, as shown at step 314. In one example, the samples may be centrifuged at 1100 to 3600 revolutions per minute (rpm) for 10 to 15 minutes cycles. In another example, the samples may be centrifuged at a rate such that the centrifugal force is in the range of about 8-12,000 g (e.g., about 10,000 g) for 15-45 minutes or 20-30 minutes. The centrifuge may be ramped up or gradually accelerated to the speed needed to create a centrifugal force in the range of about 8-12,000 g (e.g., about 10,000 g). It is further contemplated that the centrifuge may also be slowly ramped down or decelerated when the centrifugation process is complete. In some instances, it may be desirable to decelerate the centrifuge as slowly as possible so that the return to atmospheric pressure is slow so as to protect the bacterial cells from potentially bursting. The supernatant is removed and the remaining material in the tube is the purified intermediate MRT composition. This may result in a product that has been concentrated by approximately 60%.

In some instances, the centrifugation process may be a 2-tiered process. For example, the product may first undergo a "pre-spin", (for example 300 g for 2-5 minutes) to remove fecal fibrous material and then may undergo a longer centrifugation to concentrate the product. It is further contemplated that volumes of up to 300 mL may be centrifuged without resulting in a drop in the amount of concentration. In some instances, volumes of greater than 300 mL may be centrifuged. For example, as discussed above, the centrifuge volume may be selected as a percentage (for example, in the range of 60%) of the container volume. The resulting MRT composition is a bacterial suspension having a particle size of 70 $\mu m$ or less and a bacterial concentration on the order of approximately $1\times10^{10}$ CFU/g. The purified intermediate bacterial viability may be measured via a propidium monoazide (PMA) quantitative polymerase chain reaction (qPCR)

method. The resulting MRT composition may also be stable for 3 weeks at refrigeration conditions.

In some embodiments, centrifugation alone can be used multiple times for purification and concentration. However, the particle size of the bacterial suspension may still be in a range (e.g. greater than 60 µm) that clogs pipet tips. Whether this is successful or not is dependent on the input fecal material, which is variable. It is further contemplated that a system of separators and decanters could be used if the batch size was in the range of several tens of liters, or more.

The intermediate MRT composition may be optionally transferred to an intermediate tube and, if necessary, shipped to a lyophilization facility, as shown at step 316. Purified intermediate may be shipped in a pre-qualified shipper for refrigeration conditions, 5±3° C. to the contract lyophilizer, if necessary, for lyophilization.

The purified intermediate may be mixed at a 1:1 ratio with a lyophilization excipient solution, as shown at step 318. The lyophilization excipient solution may be comprised of 2.3% PEG 3350, 1% glycerin, 10% trehalose, and 10% sucrose. However, other lyophilization excipients may be used. Prior to adding the excipient solution to the purified intermediate, the lyophilization excipient solution (without glycerin) is filtered through a 0.2 µm filter. The glycerin is autoclaved at 121° C. for a minimum of 15 minutes and added aseptically. Once the lyophilization excipients and purified intermediate have been mixed (lyophilization suspension), a single two hundred microliter (200 µL) aliquot of the lyophilization suspension is placed in each well of a 96-well plate, as shown at step 320 and lyophilized, as shown at step 322.

The lyophilization process will be described with further reference to FIG. 5, which illustrates a flow chart of an illustrative lyophilization process 220/322. To perform the lyophilization, once filled, the 96-well plate may be wrapped in sterile bioshield, as shown at step 402. Other plate sizes are also contemplated. In some embodiments, a tray having zero wells may also be used. This may maximize the volume available to receive the lyophilized suspension, which may increase efficiency in the lyophilization process. After all plates are wrapped, they may be immediately transported and loaded into the lyophilizer, as shown at step 404. The lyophilizer may be sealed and the lyophilization cycle initiated. Product is frozen by lowering the product shelf temperature to a range of approximately −40° C. to −45° C., as shown at step 406. After the product is frozen, primary drying (sublimation) occurs by applying vacuum and elevating the shelf temperature up to 0° C., as shown at step 408. A secondary drying step is initiated to further reduce water content and bring the product to ambient temperature (approximately 25° C.), as shown at step 410. The vacuum is released at the end of the secondary drying step and the product is removed from the lyophilizer, as shown at step 412. Product may be placed inside an anaerobic chamber for collection of the lyophilized aliquots. The lyophilized aliquots may be in pellet form and are transferred to a packaging with desiccant, as shown at step 414. Filled packages may be purged with nitrogen gas and heat-sealed, as shown at step 416. Returning now to FIG. 4, if the intermediate MRT composition has been shipped off-site for lyophilization, the lyophilized pellets may then be shipped back to the MRT composition manufacturer, in a pre-qualified shipper for refrigeration conditions, as shown at step 324.

In some instances, it may be desirable for the lyophilized pellets to have a glass transition temperature ($T_g$) of greater than 30° C. In some examples, the glass transition temperature may be in the range of 30-75° C. This may result in a final product that is stable at room temperature. The glass transition temperature may also be used as a tool for screening the product received form the lyophilization process and/or for verifying the stablility of the final product. For example, the $T_g$ may be used to predict stability of the product during storage. In some instances, a $T_g$ of 50° C. above the storage temperature may allow the lyophilized intermediate and/or the final oral drug product to be stored for a period of time without a significant loss of bacteria.

Upon receipt of the lyophilized intermediate, it may be removed from the packaging and filled into capsules, as shown at step 326. The lyophilized intermediate may also be sampled and the total viability is measured via a PMA-qPCR method. Encapsulation may be conducted in a nitrogen-purged area at ambient temperature to minimize the exposure of the lyophilized intermediate to oxygen. The lyophilization intermediates are encapsulated in one or more hypromellose capsules. Multiple lyophilized intermediates (e.g. multiple pellets) can be loaded into a hypromellose capsule depending on the capsule size (e.g., sizes 1, 0, or 00).

The capsule may then be banded, as shown at step 328. In some instances, the capsules may be banded with hypromellose. In some instances, the banding material may be Eudragit L100, hypromellose phthalate, or hypromellose acetate/succinate. These are just examples. The banding material may be any material which is resistant to low pH environments (e.g. the stomach) and degrades in high pH environments (e.g. the intestinal tract). A consistent banding thickness is applied to each capsule so the disintegration performance meets the acceptance limit. Capsules are stored at refrigeration conditions, 5±3° C. in a nitrogen-purged bulk plastic container or packaged with desiccant. Encapsulated and banded drug product may be packaged with desiccant and heat-sealed, as shown at step 330. In some instances, the encapsulated and banded drug product may be packaged in individual dosage quantities in metallized polyester/polyethylene bonded film. This may minimize the exposure of the drug product to oxygen and/or moisture which may cause degradation of the product. The metallized polyester/polyethylene bonded film may have a moisture vapor transmission rate of 0.02 gr/100 in$^2$ and an oxygen transmission rate of 0.0402/mL/100 in$^2$ in 24 hours. The bonded film packets may be provided to the patient in a child-resistant container to meet the need for child-resistant clinical supply packaging. The child-resistant container may be a 40 dram (2.5 ounces) green pharmacy vial with a child-resistant cap. The vial may be made of translucent, light resistant polypropylene. The low density polyethylene (LDPE) child-resistant cap helps prevent unauthorized access by requiring that the user push down and rotate the cap to open the container.

EXAMPLES

The disclosure may be further clarified by reference to the following Examples, which serve to exemplify some embodiments, and not to limit the disclosure.

Example 1: Determination of Collapse Temperatures for MRT Sample Formulations

The collapse temperature results for twelve sample microbiotia restorative therapy formulations were identified. The collapse temperature may be used to assist in developing optimal formulations and lyophilization cycle parameters to freeze-dry this type of product in a reasonable amount of time without compromising its physical or chemical integrity. A standard lyophilization cycle was executed for these formulations and contained anaerobic microbial cell suspensions.

Example 2: Materials and Methods for Freeze Dry Microscopy

Twelve formulations were utilized for testing. Each base consisted of skim milk 10%, ascorbic acid 1%, gelatin 1.4% and charcoal 0.3%. Ingredients were food grade, USP or NF grade chemicals. The base was then supplemented with each of the following additives:
Trehalose 10% and Sucrose 10%
Sucrose 10% and Inositol 5%
Trehalose 10% and Glycerol 1%
Raffinose 10% and Inositol 5%
Raffinose 10% and Glycerol 1%
Glucose 5% and Inositol 5%
PEG 1% and Sucrose 10%
PEG 1% and Glycerol 1%
Trehalose 10%, Sucrose 10% and Glycerol 1%
Sucrose 10% and Lactose 8%
Trehalose 10% and Inositol 5%
PEG 1% and Lactose 8%

The formulations were prepared. The freeze-dry microscopy instrument consisted of a Olympus BX53 polarized light microscope with a Linkam FDCS196 thermal stage, a T 95 system controller, a LNP liquid nitrogen pump, and an Edwards E2M1.5 vacuum pump.

A 20 microliter (µL) aliquot of a 100 milliliter (ml) sample was placed on a glass slide which had been placed on the thermal stage after applying a small drop of silicone oil. A small coverslip was placed over the sample and the chamber was sealed. The sample was then cooled to −45 degree Celsius (° C.) at 10° C./minute. The temperature at which the material became frozen during the cooling stage was recorded. Once the temperature dropped to −45° C., the vacuum was initiated. The product sample was then warmed at 1° C./minute. The product sample was monitored continuously during the cycle to observe the drying and sublimation fronts. Once evidence of collapse was observed the temperature was recorded. Table 3 is a summary of the freezing temperature and the collapse temperature for each of the formulations.

TABLE 3

Freezing temperatures and collapse temperatures recorded for each formulation.

| Formulation | Freezing Temperature | Collapse Temperature |
| --- | --- | --- |
| Trehalose and Sucrose | −20° C. | −24° C. |
| Sucrose and Inositol | −15° C. | −20° C. |
| Trehalose and Glycerol | −16° C. | −24° C. |
| Raffinose and Inositol | −22° C. | −22° C. |
| Raffinose and Glycerol | −18° C. | −26° C. |
| Glucose and Inositol | −13° C. | −23° C. |
| PEG and Sucrose | −11° C. | −23° C. |
| PEG and Glycerol | −12° C. | −22° C. |
| Trehalose, Sucrose and Glycerol | −16° C. | −26° C. |
| Sucrose and Lactose | −17° C. | −25° C. |
| Trehalose and Inositol | −16° C. | −25° C. |
| PEG and Lactose | −17° C. | −20° C. |

Lyophilization cycles are influenced by a variety of factors including percent solids in the formulations, vial size and diameter, collapse temperatures, chamber pressures, shelf temperatures, product resistance, etc. The chamber pressure and shelf temperature necessary to complete the primary drying process is determined by the thermal characteristics of the formulation, mainly the collapse temperature. The primary drying temperature is colder than the collapse temperature to account for product warming that occurs from increased resistance from the growing dried layer. Three cycles were designed based on the combination of factors above. All cycle times were less than 48 hours to complete. Table 4 is a summary of the drying temperature and chamber pressures for the lyophilization cycles based on critical collapse temperatures.

TABLE 4

Primary drying temperatures and chamber pressures for the Lyophilization cycles based on critical collapse temperatures.

| Critical Temperature | Primary Drying Temperature | Chamber Pressure |
| --- | --- | --- |
| −20° C. to −22° C. | −30° C. | 120 mTorr |
| −23° C. to −24° C. | −33° C. | 95 mTorr |
| −25° C. to −26° C. | −35° C. | 75 mTorr |

A lyophilization cycle was designed based on data collected during the freeze dry microscopy studies. A pilot lyophilization cycle was conducted for each of the formulations to test for cake structure and survival of a bacterial cell mixture. Harvesting of cells and dispensing of the suspension were completed based on protocols established by Gibson Bioscience to obtain microbial ranges of 10e7 to 10e8 colony forming units per 100 microliter aliquot of the mix. The microorganism stocks used were selected from the first phase of the study and included the following anaerobes: *Bacteroides uniformis* ATCC 8492™, *Alistipes putredinis* ATCC 29800™, *Ruminococcus gnavus* ATCC 29149™ and *Bacteroides ovatus* ATCC 8484™.

The number of viable cells (CFU) before and after lyophilization was determined by serial dilution method. Dilutions consisted of the following levels: 10e3, 10e5, 10e7, and 10e9. Pellet samples were rehydrated in 1 mL of Phosphate Buffered Saline. All samples were plated to pre-reduced CDC Anaerobic Blood Agar and selective *Bacteroides* Bile Esculin Agar in duplicate. Agar plates were incubated at 35-37° C. for 48 hours in an anaerobic atmosphere.

The lyophilization cycles produced good quality cake structures for all formulations. Pellets were solid and uniform in appearance. Each lyophilized pellet dissolved within 30 seconds upon rehydration in 1.0 mL of Phosphate Buffered Saline. Survival rates were calculated as a percentage of the total number of bacterial colony forming units after freeze-drying divided by the total number of bacterial colony forming units before freeze-drying. Colony Forming Units were based on the mix of the 4 organisms. The viability and percent survival of total colony forming units for each formulation are summarized in Tables 5 and 6.

TABLE 5

Viability and percent survival of total colony forming units for each formulation inoculated directly to CDC Anaerobic Blood Agar.

| Formulation | Total CFU Pre-Lyophilization | Total CFU Post-Lyophilization | Percent Survival* |
| --- | --- | --- | --- |
| Trehalose, Sucrose, Glycerol | 2.10E+08 | 9.05E+07 | 95.61% |
| Trehalose, Inositol | 5.65E+08 | 5.00E+07 | 87.97% |

TABLE 5-continued

Viability and percent survival of total colony forming units for each formulation inoculated directly to CDC Anaerobic Blood Agar.

| Formulation | Total CFU Pre-Lyoph- ilization | Total CFU Post-Lyoph- ilization | Percent Survival* |
|---|---|---|---|
| Sucrose, Lactose | 1.70E+08 | 1.30E+08 | 98.58% |
| Trehalose, Sucrose | 5.15E+08 | 4.95E+08 | 99.80% |
| Sucrose, Inositol | 6.30E+07 | 6.00E+07 | 99.73% |
| Raffinose, Inositol | 3.40E+08 | 2.85E+08 | 99.10% |
| Trehalose, Glycerol | 3.00E+08 | 1.30E+08 | 95.72% |
| Raffinose, Glycerol | 3.65E+08 | 2.25E+08 | 97.55% |
| PEG, Sucrose | 1.05E+08 | 6.10E+07 | 97.23% |
| Glucose, Inositol | 2.17E+09 | 4.05E+08 | 92.19% |
| PEG, Lactose | 3.10E+08 | 2.40E+08 | 98.69% |
| PEG, Glycerol | 4.15E+08 | 3.25E+08 | 98.77% |

*Based on Log Transformed Data

TABLE 6

Viability and percent survival of total colony forming units for each formulation inoculated directly to selective *Bacteroides* Bile Esculin Agar.

| Formulation | Total CFU Pre-Lyo | Total CFU Post-Lyo | Percent Survival* |
|---|---|---|---|
| Trehalose, Sucrose, Glycerol | 1.26E+07 | 2.75E+06 | 90.69% |
| Trehalose, Inositol | 1.95E+08 | 4.05E+05 | 67.64% |
| Sucrose, Lactose | 1.37E+07 | 1.00E+05 | 70.06% |
| Trehalose, Sucrose | 2.45E+07 | 2.42E+07 | 99.92% |
| Sucrose, Inositol | 1.35E+07 | 1.02E+07 | 98.29% |
| Raffinose, Inositol | 7.50E+07 | 1.00E+06 | 76.19% |
| Trehalose, Glycerol | 8.05E+07 | 7.50E+05 | 74.31% |
| Raffinose, Glycerol | 3.00E+07 | 1.00E+04 | 53.50% |
| PEG, Sucrose | 1.05E+07 | 5.55E+05 | 81.81% |
| Glucose, Inositol | 4.50E+07 | 9.00E+05 | 77.80% |
| PEG, Lactose | 1.25E+07 | 1.50E+05 | 72.93% |
| PEG, Glycerol | 7.10E+07 | 1.15E+04 | 51.72% |

*Based on Log Transformed Data

Based on the data collected, the selected anaerobes showed the highest survival rate when the combination of Trehalose and Sucrose or Sucrose and Inositol were utilized in the base formulation. This was true for recovery on both CDC Anaerobic Blood Agar and selective *Bacteroides* Bile Esculin Agar. These results indicate that the combination of Trehalose and Sucrose or Sucrose and Inositol provide the best protection for *Bacteroides* sp. during lyophilization.

Example 3: Bacterial Stability of Solid Product During Storage

A study was preformed to determine the stability of the packaged encapsulated capsule after manufacturing and upon storage. A standard microbiological plating method, a molecular non-culture PMA-qPCR method, and 16s rRNA gene sequencing of both PMA and non-PMA treated samples were employed to characterize the active component (bacteria) present in the solid drug product. The plating and total viability stability data indicate that a lyophilized packaged, encapsulated product (using a first lyophilization process) is more stable at colder storage conditions (5±3° C.) than at higher storage temperatures and relative humidity (25±2° C./60%±5% RH and 30±2° C./65%±5% RH). The plating and total viability stability data for a lyophilized packaged, encapsulated product (using a second lyophilization process) indicates that packaged, encapsulated product is stable at both 5±3° C. and 25±2° C. storage temperatures.

It should be understood that this disclosure is, in many respects, only illustrative. Changes may be made in details, particularly in matters of shape, size, and arrangement of steps without exceeding the scope of the disclosure. The invention's scope is, of course, defined in the language in which the appended claims are expressed.

What is claimed is:

1. A packaged pharmaceutical product, comprising:
   a package;
   one or more capsules disposed in the package; and
   a lyophilized material disposed within each of the one or more capsules, the lyophilized material comprising:
      fecal microbiota, and
      a lyophilization excipient, wherein the lyophilization excipient comprises polyethylene glycol, and one or more selected from trehalose, sucrose, and glycerin.

2. The packaged pharmaceutical product of claim 1, wherein the package comprises a blister pack.

3. The packaged pharmaceutical product of claim 1, wherein the package includes an oxygen scavenger disposed in the package.

4. The packaged pharmaceutical product of claim 1, wherein the package includes a desiccant disposed in the package.

5. The packaged pharmaceutical product of claim 1, wherein the package comprises a metallized polyester/polyethylene bonded film.

6. The packaged pharmaceutical product of claim 1, wherein the package has a vapor transmission rate of 0.02 gr/100 in² in 24 hours.

7. The packaged pharmaceutical product of claim 1, wherein the package has an oxygen transmission rate of 0.0402 gr/100 in² in 24 hours.

8. The packaged pharmaceutical product of claim 1, wherein the lyophilized material comprises a lyophilization excipient comprising two or more selected from trehalose, sucrose, and glycerin.

9. The packaged pharmaceutical product of claim 1, wherein the lyophilized material comprises a lyophilization excipient comprising trehalose, sucrose, and glycerin.

10. A packaged pharmaceutical product, comprising:
    a metallized film package;
    a plurality of capsules disposed in the metallized film package; and
    a lyophilized material disposed within each of the capsules, the lyophilized material comprising:
       fecal microbiota, and
       a lyophilization excipient, wherein the lyophilization excipient comprises polyethylene glycol, and one or more selected from trehalose, sucrose, and glycerin.

11. The packaged pharmaceutical product of claim 10, wherein the lyophilized material comprises a lyophilization excipient comprising two or more selected from trehalose, sucrose, and glycerin.

12. The packaged pharmaceutical product of claim 10, wherein the lyophilized material comprises a lyophilization excipient comprising trehalose, sucrose, and glycerin.

13. A microbiota restoration therapy composition, comprising:
    a capsule; and
    a lyophilized material disposed within the capsule, the lyophilized material comprising fecal microbiota, and a lyophilization excipient comprising polyethylene glycol, trehalose, sucrose, and glycerin.

14. The microbiota restoration therapy composition of claim 13, wherein the lyophilized material has a glass transition temperature greater than 30° C.

15. The microbiota restoration therapy composition of claim 13, wherein the lyophilized material has a glass transition temperature in the range of 30-75° C.

16. The microbiota restoration therapy composition of claim 13, wherein the capsule is disposed in a blister package.

17. The microbiota restoration therapy composition of claim 13, wherein the capsule is disposed in a metallized film package.

\* \* \* \* \*